United States Patent
Farruggia et al.

(10) Patent No.: US 8,473,262 B2
(45) Date of Patent: Jun. 25, 2013

(54) SELF-CLEANING SUBMERGED INSTRUMENTATION

(75) Inventors: Guy J. Farruggia, Ellicott City, MD (US); Allan B. Fraser, Casper, WY (US); John K. Hudak, State College, PA (US)

(73) Assignee: Areté Associates, Northridge, CA (US)

( * ) Notice: Subject to any disclaimer, the term of this patent is extended or adjusted under 35 U.S.C. 154(b) by 1005 days.

(21) Appl. No.: 12/228,687

(22) Filed: Aug. 14, 2008

(65) Prior Publication Data

US 2010/0042389 A1    Feb. 18, 2010

(51) Int. Cl.
*G06F 13/00* (2006.01)
*G01H 13/00* (2006.01)

(52) U.S. Cl.
USPC ........................................ 703/2; 703/7; 703/9

(58) Field of Classification Search
USPC ...... 703/7, 9; 73/570, 579; 366/127; 396/127
See application file for complete search history.

(56) References Cited

U.S. PATENT DOCUMENTS

| | | | |
|---|---|---|---|
| 4,092,858 A | 6/1978 | Edgerton | |
| 4,170,185 A | 10/1979 | Murphy et al. | |
| 4,375,991 A * | 3/1983 | Sachs et al. | 134/1 |
| 4,763,537 A * | 8/1988 | Scott et al. | 73/170.29 |
| 5,162,077 A | 11/1992 | Bryan et al. | |
| 5,384,029 A | 1/1995 | Campbell | |
| 5,539,209 A | 7/1996 | Maarschalkerweerd | |
| 5,889,209 A * | 3/1999 | Piedrahita et al. | 73/570 |
| 6,880,402 B1 * | 4/2005 | Couet et al. | 73/579 |
| 7,579,077 B2 * | 8/2009 | Dubrow et al. | 428/357 |
| 7,942,568 B1 * | 5/2011 | Branch et al. | 366/127 |
| 2010/0285972 A1 * | 11/2010 | Dubrow et al. | 506/7 |

FOREIGN PATENT DOCUMENTS

| | | |
|---|---|---|
| FR | 2832082 | 5/2003 |
| JP | 2005274216 | 10/2005 |

\* cited by examiner

*Primary Examiner* — Thai Phan
(74) *Attorney, Agent, or Firm* — Peter I. Lippman

(57) ABSTRACT

Techniques and apparatus inhibit, limit, or remove biofouling and certain inorganic accumulations, to increase the longevity of accurate in-situ oceanographic and other underwater measurements and transducing processes. The invention deters formation of an initial bacterial layer and other precipitation, without harming the environment. The invention integrates an ultrasonic source into a sensor or other device, or its supporting structures. The ultrasonic source vibrates one or more critical surfaces of the device at a frequency and amplitude that dislodge early accumulations, thus preventing the rest of the fouling sequence. The ultrasonic driver is activated for short periods and low duty cycles, and in some cases preferably while the device is not operating.

67 Claims, 18 Drawing Sheets

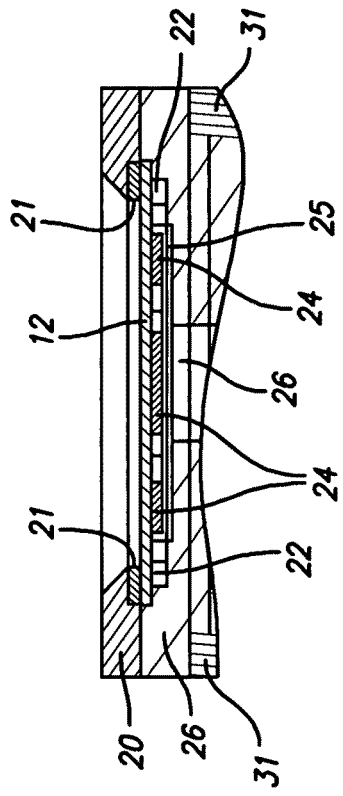
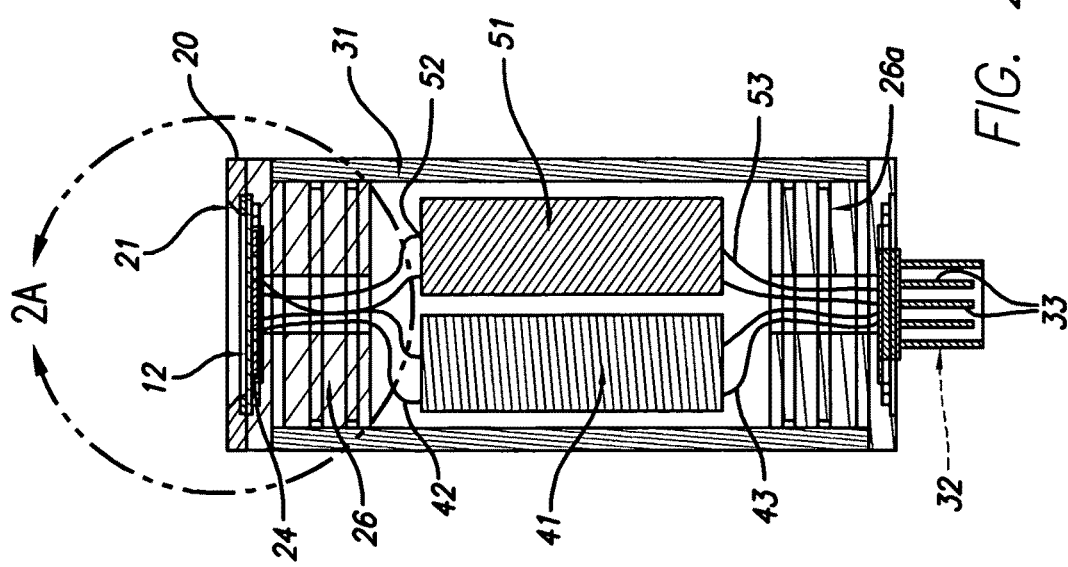
FIG. 2A
FIG. 2

SELF-CLEANING SUBMERGED INSTRUMENTATION

RELATION BACK

This document is in part based upon and claims priority of U.S. Provisional Application 60/773,578 filed Feb. 14, 2006, and of the corresponding international application PCT/US07/003914 filed Feb. 13, 2007, in the names of the present inventors. This document thus constitutes the national phase, and when appropriate may be denominated a continuation-in-part, of that PCT application.

FIELD OF THE INVENTION

This invention relates generally to removing or preventing biofouling or other accumulation of detritus on active surfaces of submerged systems—and more specifically to doing so without impacting the surrounding ecological environment.

Currently "biofouling" or biological fouling is defined in Wikipedia® as, in part:

"undesirable accumulation of microorganisms, plants, algae, and animals on submerged structures, especially ships' hulls . . . . In the same manner it is found as fouling in cooling water cycles of large industrial equipments and power stations."

The word is also the name of an international, multidisciplinary journal dealing with these topics. Thus the invention relates to enhancing longevity and performance of submerged measuring instruments and many other devices, by fending off disruptions that biofouling poses to operation of such equipment.

Much of our own interest is in combined sensors for measuring conductivity and temperature in the ocean—but also in other waters. This document therefore focuses largely on such apparatus; however, such measuring equipment and methods are also intended to serve as examples of the much broader areas of application in which the invention can be used.

That is, certain aspects of the invention are not limited to oceanographic work, or to other systems for use in naturally occurring waters, or even to measuring instruments. Although we are particularly interested in curbing organisms that occur in water, some biological forms occur and can flourish in nonaqueous liquids, and in colloids and gels as well.

BACKGROUND

Many organisms live on and disrupt devices in lakes, rivers and streams, in potable-water reservoirs, tanks, aqueducts and piping, and in industrial chemical-process plants and vats—as well as in the ocean. Our invention is beneficial for virtually every natural and artificial environment in which biofouling or other accumulations of liquid-borne materials (including nonbiological materials) disrupt or degrade equipment operations.

Thus we ask that the reader consider the following discussions as both (1) specific to the control of biofouling in seawater conductivity and temperature measurement, and (2) exemplary of the restraint of many other disruptive aggregations in liquids.

Thus the invention has broadly applicable capabilities in all these circumstances.

Both new and established observational approaches are being used for advancing fundamental understanding, monitoring, modeling, and management of the ocean environment. The ocean is tremendously complex, with countless disparate variables, each with a large range of scales. Scientific data are required at relatively high sampling frequencies and accuracies for long periods with minimal drift from calibrations. The infrastructures for such observations are developing rapidly and will include numerous dedicated oceanic observational systems. These systems will capitalize on moorings, autonomous underwater vehicles (AUVs), gliders, drifters and profiling floats.

Biofouling is a significant limitation for in-situ measurements in the coastal ocean specifically, and the whole ocean generally. Biofouling can degrade sensor accuracy and performance in a very short time, especially for contact sensors with exposed transducers and optical sensors with exposed windows. In general, for exposed windows to function adequately they must be unobstructed; this is essentially true for windows intended to transmit acoustic vibrations as well as windows intended for electromagnetic radiation. Biofouling is well known to be one of the primary limiting factors in measurement accuracy and deployment longevity for long-term oceanographic studies.

Bacteria rapidly colonize surfaces that are in contact with water. This first step of biofouling is detrimental to immersed sensing systems, as well as to industrial processes and man-made structures. The exact mechanisms of the bacterial surface colonization, particularly during its initial stages, are not fully understood. It is known, however, that once this rather fine biofilm has been established on a submerged surface, further colonization leading to biofouling by higher organisms proceeds. In advanced stages of biofouling numerous organisms degrade submerged, moored, or slowly moving sensors and measurement systems.

Attempts to solve the problem of biofouling of oceanographic sensors have used a wide variety of antifouling approaches. Various biotoxic or bioinhibiting products based on tributyl-tin (TBT) have traditionally been used to prevent fouling in longterm oceanographic instrumentation deployments. The toxic effects of TBT on mammals and the bioaccumulation of TBT in fish, oysters, and crustaceans have severely limited its longterm usefulness as a marine antifoulant. TBT-based antifoulant wax (Aquatek) and Clear-Choice aerosol spray, a polymer-based tributyl-tin methacrylate (ITW Philadelphia Resins) have been applied to areas surrounding the windows of optical instruments. Although these products are somewhat effective against algal growth, generally they are not applied directly to optical surfaces because they introduce deleterious scattering and refractive-noise errors. Ironically the roughness of these bioinhibiting coatings may provide stronger attachment for microorganisms than smooth surfaces. Additional limitations of the biodeterrent coatings include perturbed spectral transmission (window clouding) and flaking off of coatings caused by ablation. TBT compounds also have a direct negative environmental impact, as TBT is extremely toxic and should never be deliberately placed in natural waters.

Other biotoxic agents used in this field include a slowly dissolving chlorine source (trichlorisocyanuric acid); and bromine-producing tablets have been utilized in closed optical systems. These chemicals are toxic to microorganisms, preventing growth in the optical tubes. Alconox, a powdered cleaning compound (homogeneous blend of sodium dodecyl-benzyl sulfonate, phosphates, and carbonates), has also been used in this manner to prohibit algal growth on optical windows.

Other such antifoulant methods for general nonoptical sensors have been used with limited success. A mixture of cayenne pepper with silicone-based grease applied to the heads of an acoustic Doppler current profiler (ADCP) helped inhibit biological growth on a bottom-mounted tripod. Upon recovery of the ADCP, extensive growth of bryozoans was noted. These animals, members of a large class of marine creatures prominent in fossils, had grown on all exposed areas of the ADCP except for the acoustic heads. Coatings of grease and pepper are not suited for optical sensors.

Zinc anodes on stainless-steel instrument cages inhibit biological growth on the stainless-steel parts. This simple and otherwise useful technique has limited application in a full antifouling approach.

Historically, copper was used extensively to protect wooden-hulled vessels from shipworms (mollusks, genus *Teredo*) and wood-boring crustaceans (genus *Limnoria*). More recently copper has been used effectively for inhibiting the growth of foulants on sensors. Copper interferes with enzymes on cell membranes and prevents cell division. As copper corrodes in seawater, copper ions are released into the water. Importantly, while copper ions are toxic at high concentrations for most organisms, they are not toxic to humans in the concentrations caused by the copper antifoulants—in contrast to TBT. Copper shutters, screens and plates have been used with some effectiveness on underwater optical sensors (Satlantic). There are numerous mechanical limitations, however, when using moving copper parts in optical systems.

Biofouling adversely affects the accuracy of electrical conductivity measurements. The contact resistances of conductivity cells change when a biofilm is deposited on its exposed surfaces. Some contact conductivity sensors use flow-through configurations, putting them at a significant disadvantage in terms of fouling. When not obstructed, these devices are known for their accuracy and stability and are standards in the industry. A conductivity sensor that uses a long flow-through tube and large electrodes to achieve its standard-setting accuracy is degraded quickly in a biofouling environment.

Some manufacturers use an inductive cell—which can be less susceptible to fouling since it has no electrodes. Such a conductivity sensor requires flow through a confined path, however, and is prone to detritus buildup and performance degradation. All such sensors could directly benefit from use of our invention to remove or prevent fouling.

Some workers in relatively remote fields have attempted to clean e.g. medical appliances by transmitted vibration; see e.g. U.S. Pat. Nos. 4,906,238 and 4,698,058. In addition to the remoteness of the fields, those proposals have been in the public eye for nearly two decades now, and are not believed to have been followed or commercially exploited.

Slightly more relevant are U.S. Pat. No. 5,384,029 of Campbell and French application 2,832,082 of Colas, assigned to Sedia, which both teach using a piezoelectric transducer for agitating or "stirring" the test fluid and cleaning the outer surface of a membrane that seals the transducer cavity—thus minimizing interference with the operation of a sensor that quantifies the presence of dissolved gas (e.g. oxygen) in wastewater or like liquid medium. Likewise relevant are European patent application 1,134,577 of Trainoff, assigned to Wyatt Technology Corporation and relating to cleaning the interior of a flow-through optical cell; U.S. Pat. No. 4,170,185 of Murphy, assigned to Lectret S. A. and directed to preventing marine fouling of a boat; and U.S. Pat. No. 5,724,186 of Collier, which concerns removing raindrops from automotive side-view mirrors.

Among several significant differences between these five references and the environments of interest to the present inventors is that none of these prior documents involves cleaning of either an active transducing surface of a sensor, or a rigid window surface for transmitting electromagnetic radiation or acoustic vibration. Other important distinctions will be seen later in this document. These twin problems of biofouling and chemical deposition have been well known for at least a half-century, but—as will also be seen—the present invention is the first to deal with either problem in a fully effective way.

To reduce the interfering effects of interfacial contact impedance, conductivity electrodes are typically platinized—that is, electrodeposited with a layer of mossy and weakly adhering microparticles of platinum. Such layers have dendritic structures, and due to their black appearance they are commonly called "platinum black." Platinizing increases the electrode surface area greatly, thereby reducing the contact impedance of the electrode-electrolyte interface.

As can be now understood, the prior art does provide useful capabilities of measuring instruments and other equipment in immersed environments. Nevertheless the art has left important refinements to be desired in the area of longevity of measuring apparatus for best performance underwater, and likewise more generally longevity of other types of devices and other liquid environments.

SUMMARY OF THE DISCLOSURE

The present invention provides just such refinement. The invention has several aspects or facets, that can be practiced independently; however, for fullest enjoyment of their benefits as will be seen at least some of the various facets of the invention are preferably used together in combination.

In preferred embodiments of its first major independent facet or aspect, the invention is apparatus for use with a device which has an exposed surface, as follows. The surface is either:

an exposed window surface, or
an exposed active transducing surface that is part of a transducer and is outside any sealed chamber that may be associated with the device.

In addition, the surface is (a) critical to performance of the device and (b) operated at least partially submerged within and in direct contact with an aqueous medium, and (c) susceptible to biofouling.

From the above wording "for use with a device", it is to be understood that in this partial statement of the first facet of the invention the "device" and its "surface" are not elements of the inventive apparatus itself. Rather they are only parts of the context, or environment, of the invention. This is an important distinction, since—when embodied in certain of the appended claims—it controls what kinds of activity will prima facie constitute infringement.

Further to this distinction, it will be noted that in certain of the appended claims, in the bodies of the claims, the word "such" is used as a definite article—instead of "the" or "said"—when referring back to features of the environment of the invention that are introduced in the claim preambles. The purpose of this special nomenclature is to assist in most clearly emphasizing which features are actually elements of the invention as claimed, and which are parts of the context or environment in which the invention is used. Thus this terminology strongly promotes the desirable objective of the claims, to "particularly point out and distinctly claim" the invention.

References to "aqueous medium" throughout this document reflect some of our present most-highly-preferred forms of the invention. We wish to make plain, however, that our invention is not thus limited. It also encompasses usages of the invention with nonaqueous media instead. As will be clear, certain of the appended claims may be directed to such usages.

Now continuing discussion of the first aspect or facet of the invention (bearing in mind the foregoing statements about the context or environment of the invention): The inventive apparatus itself includes an ultrasonic cleaning system operative at a frequency or frequencies in a range of approximately twenty kilohertz to nearly four hundred kilohertz. It also includes some means for substantially directly fixing the system to (or integrating the system into) the above-mentioned surface, to vibrate that surface and thereby reduce or substantially eliminate biofouling of the surface—particularly formation of biofilm on the surface.

The foregoing may represent a description or definition of the first aspect or facet of the invention in its broadest or most general form. Even as couched in these broad terms, however, it can be seen that this facet of the invention importantly advances the art.

In particular, this facet of the invention extends the optimum high-performance life of many kinds of submerged apparatus from a range between a few hours and a few days to a range on the order of months or years. In principle the optimum-performance life of such apparatus may be indefinite, limited only by the continuing operation of the cleaning system that reduces or substantially eliminates organisms on the surface.

Although the first major aspect of the invention thus significantly advances the art, nevertheless to optimize enjoyment of its benefits preferably the invention is practiced in conjunction with certain additional features or characteristics. In particular, preferably the apparatus of the first aspect of the invention includes (I.e. is claimed in combination with) the device to be cleaned, including the critical surface.

In other words, whereas the apparatus of the first facet of the invention as most broadly defined above expressly excludes the device and critical surface, the preferred combination as defined here is the opposite. (A like distinction appears in certain of the appended claims.) If this basic, or main, preference for including the device and its critical surface is observed, then further preferences (or "subpreferences") are that:

the window (if the surface is a window) be rigid, and transmissive of electromagnetic radiation or acoustic vibration—and that the system be fixed to or integrated into the surface at a part of the device that is behind (in other words, in back of) the exposed window surface; or the active transducing surface (if the surface is "active transducing") be in direct contact with the aqueous medium outside any such sealed chamber—and the transducing surface interacts directly with a characteristic or constituent of the aqueous medium, to develop signals indicative of a parameter of such characteristic or constituent.

In either case, we prefer that the system be fixed to or integrated into the surface at a part of the device that is behind (in other words, in back of) the exposed window surface. In the second case introduced just above, we are particularly interested in two subcases:

that the "characteristics" are the low-frequency electrical conductivity and temperature, and the "parameter" is the salinity or density (or both) of the aqueous medium—in this sub-case we further prefer that the active transducing surface interact directly with the ionic species in the liquid medium (most commonly electrochemically); and that the "constituent" is a chemical species, while the "parameter" is concentration of the species—in this sub-case we further prefer that the active transducing surface interact directly with the chemical species in the liquid medium electrochemically.

In both these just-enumerated subcases we further prefer that the transducer measuring the electrical conductivity have electrodes, which also are exposed in the aqueous medium and susceptible to biofouling, and further that the cleaning system reduce or substantially eliminate biofouling of these electrodes in addition to biofouling of the surface.

(For purposes of this document, but most particularly in the claims, the term "substantially" is used primarily, though not exclusively, to encompass variants in which the recited characteristic—e.g., here "eliminates biofouling"—is absent only because of an infringer's attempt to avoid the claim language through trivial or inconsequential modifications. Such usages of the word "substantially" are thus intended to bring infringing behavior within the literal language of the claims, rather than resorting to the patent Doctrine of Equivalents.)

Another basic preference is that the cleaning system be unitary with the device.

Another main preference is that the fixing-or-integrating means include a substantially solid vibration-transmitting structure intermediate between that surface and the cleaning system. In this case a subpreference is that the structure include a mounting plate fixed between the surface and the cleaning system.

Still other preferences are that:
the fixing-or-integrating means include a coupling gel or adhesive for transferring vibration from the cleaning system to such surface;
the fixing-or-integrating means include a substantially solid intermediate structure, and a coupling gel or adhesive for transferring vibration from the cleaning system to the surface;
the fixing-or-integrating means are not for transmitting vibration to the surface through the aqueous medium that surrounds the surface (it will be understood, however, that some vibration may pass to the surface through that medium notwithstanding that this is not the intended function of the fixing-or-integrating means—and in general such stray vibration paths are not harmful to the overall function of such embodiments of our invention);
the fixing-or-integrating means include a portion of the device;
the device be exposed within a fouling environment and include an optical component, or a passive or active transducer;
the device is an electrical- or thermal-conductivity sensor; or a sensor of oxygen or pH, or other chemical sensor; or a window for passing electromagnetic radiation; or a compressive-wave transducer that is not itself self cleaning; or a solar panel; or an antenna.

If the device is in this last-mentioned list, then further sub-preferences are that:
the device be a window or other element, at least part of which is not to be obstructed, the ultrasonic cleaning system comprise an ultrasonic element that is toroidal—positioned generally along the periphery of the window or other element—or is otherwise peripheral to such window or other element, and does not obstruct the not-to-be-obstructed part of such window or other element; or alternatively the surface can be obstructed without impairing its function, and the ultrasonic cleaning system comprise an ultrasonic element that is for mounting generally centrally to such surface.

Another set of alternative preferences is that the ultrasonic cleaning system include a driver that is:
- a piezotransducer, operating at a frequency or frequencies in a first frequency range of approximately fifty kilohertz to nearly four hundred kilohertz, or
- an electrostatic driver operative at a frequency or frequencies in a second range of approximately twenty to fifty kilohertz, or
- an electromagnetic driver operating in that second range, or
- a microelectromechanical drive or other mechanical machine likewise operative in that second range.

If any of these last-mentioned alternative preferences is observed, then a further subpreference is that the piezotransducer be piezoceramic, and that changes in dimension in the cleaned window or transducer be at least as large as thickening or thinning of the piezoceramic during vibration. This last-mentioned relationship is a seemingly implausible amplification capability that actually is achieved readily and very advantageous. As also a part of this same subpreference, the piezoceramic piezotransducer has relatively higher mass than piezofilm piezotransducers have, and accordingly provides higher amplitude of vibration in such surface than possible using a piezofilm piezotransducer.

Yet another basic or main preference is that the exposed transducing surface include or be part of a conductivity sensor or electrochemical sensor that is not sealed by a membrane, and the ultrasonic cleaning system and fixing-or-integrating means include some means for vibrating the surface. In this latter case further sub-preferences are that the conductivity sensor be substantially planar, and that it be built upon a ceramic substrate.

Still another basic preference is that the device include a conductivity-measuring cell that has one or more sensing elements and senses the impedance of a sensing element, or impedance between pairs of sensing elements or among groups of sensing elements, as immersed in a medium. In this regard it will be understood by those skilled in this field that what is conventionally called the impedance of a single sensing element is in reality, to speak more precisely, impedance between that sensing element and some reference component—such as electrical ground or a chassis or the like—or some otherwise established reference potential.

In this case a subpreference is that the conductivity-measuring cell determine a ratio between a voltage impressed across the cell, and a resulting current through the cell. Conversely the determined ratio may be between a current forced through the cell and a resulting voltage.

Another main preference is that, if the surface has a functional region, the ultrasonic cleaning system and fixing-or-integrating means include some means for vibrating the functional region of the surface in a particular vibrational mode whose amplitude is high enough, throughout the functional region, to effectively reduce or substantially eliminate biofouling in the functional region. In this case preferably the vibrational mode has substantially no node within the functional region.

A further main preference, if the surface has a functional region generally at or near a center of the surface, is that the ultrasonic cleaning system and fixing-or-integrating means include some means for vibrating the generally central functional region in a fundamental mode, to effectively reduce or substantially eliminate biofouling in the generally central functional region.

Also a main preference is that the ultrasonic cleaning system and fixing-or-integrating means include some means for vibrating the surface in a zero-order mode, to effectively reduce or substantially eliminate biofouling throughout the surface. Another main preference is that the cleaning system and the fixing-or-integrating means include some means for vibrating the surface in a plurality of modes, either simultaneously or separately. Such a combination of plural modes provides effective cleaning across at least a region of such surface. People skilled in this field will appreciate the reason for such effective cleaning—namely, that any point not effectively cleaned by one mode, perhaps due to being positioned near a node of the vibration, is likely to spaced well between nodes of another vibrational mode. In this case a subpreference is that the surface be mounted between two compliant elements to oscillate separately from other mounting parts of the apparatus.

Other main preferences are that:
- the vibrating means include some means for searching for a natural resonance of the surface, as mounted;
- the ultrasonic cleaning system and fixing-or-integrating means include some means for vibrating the surface at a duty cycle that is on the order of five percent, or less—and still more preferably on the order of one percent, or less, and further preferably on the order of one-tenth percent, or less;
- the apparatus further include some means defining a waterproof chamber whose interior is generally at or near atmospheric pressure, with the critical surface forming part of an external wall of the chamber—or with the active transducing surface outside the chamber.

In this last-mentioned case it is additionally preferred that the waterproof chamber contain a circuit or vibrating element, or both, of the ultrasonic cleaning system.

Yet other main preferences are that:
- the apparatus further include some means for determining ideal operating conditions of the device, and some means for automatically adjusting operating conditions of the device to substantially the determined ideal conditions;
- the apparatus further include some means for evaluating measurement output signals of the device, and some means for adjusting parameters of such signals to substantially optimize utilization of such signals;
- the apparatus also include some means for operating the cleaning system, to reduce or substantially eliminate such biofouling, when the critical surface is no longer submerged within the aqueous medium—in which case a further subpreference is that the surface form a periscope window for a craft or other apparatus that sometimes operates submerged in an aqueous medium, and the operating means include some means for vibrating the surface, selectively, while the sometimes-submerged craft or other apparatus either is submerged in the aqueous medium or after it comes to the surface;
- the apparatus also include some means for operating the cleaning system at one or more frequencies determined from the particle sizes of fouling material to be reduced or substantially eliminated—in which case a subpreference is that the operating means include some means for searching for natural resonance associated with the particle size;

the device include a conductivity-sensing cell and a temperature-measuring thermistor—with sensitive measuring fields of the conductivity cell and thermistor substantially collocated;

distance between a vibratory driver of the ultrasonic cleaning system and the surface is on the order of one centimeter, or less.

In preferred embodiments of its second major independent facet or aspect, the invention is apparatus for use with a device that has an exposed window surface or an exposed active transducing surface that is part of a transducer and is outside any sealed chamber that may be associated with the device, and is (a) critical to performance of the device and (b) operated at least partially immersed within and in direct contact with a liquid, and (c) susceptible to undesirable chemical deposition on the surface. (As before, the foregoing is related to the context or environment of the second aspect of the invention, rather than elements of this aspect of the invention itself.) The inventive apparatus itself includes an ultrasonic cleaning system that is operative at a frequency or frequencies in a range of approximately fifty to eighty kilohertz. It also includes some means for substantially directly fixing the system to or integrating the system into such critical surface, to vibrate such surface and thereby reduce or substantially eliminate such chemical deposition.

The foregoing may represent a description or definition of the second aspect or facet of the invention in its broadest or most general form. Even as couched in these broad terms, however, it can be seen that this facet of the invention importantly advances the art.

In particular, this aspect of the invention provides advantages relative to chemical deposition that are very generally analogous to the benefits described earlier with respect to organic accumulations. Chemical precipitation may derive from organisms, or may be chemicals in process-stream plants, or a great number of other sources.

Although the second major aspect of the invention thus significantly advances the art, nevertheless to optimize enjoyment of its benefits preferably the invention is practiced in conjunction with certain additional features or characteristics. In particular, most or many of the preferences presented above for the first aspect of the invention are applicable to the second as well.

For example we prefer that the apparatus be made and used in combination with the device, including the critical surface. In this case it is especially of interest that the device be particularly susceptible to undesirable deposition of calcium carbonate.

Also preferably the fixing-or-integrating means include a substantially solid vibration-transmitting structure intermediate between such surface and the cleaning system. Another preference is that the vibrating means include some means for searching for the natural resonance of the surface, as mounted.

The many other preferences discussed at great length above will not be repeated here, even though applicable here as well.

In preferred embodiments of its third major independent facet or aspect, the invention is conductivity-measuring apparatus. The apparatus includes a generally planar sensing-cell surface that, at least when operating, is exposed in an aqueous medium. It also includes, disposed on the generally planar surface:

plural ring-shaped current-drive electrodes, and voltage-sensing electrodes, each disposed within a respective one of the drive electrodes.

The voltage electrodes are offset, toward each other in pairs, from respective centers of the current electrodes.

The foregoing may represent a description or definition of the third aspect or facet of the invention in its broadest or most general form. Even as couched in these broad terms, however, it can be seen that this facet of the invention importantly advances the art.

In particular the geometry described in this document provides remarkable longterm-stable operation in a planar sensor. This third facet of the invention thereby enables excellent measurement performance with no need for flow-through sensor configurations—and no need for otherwise convoluted sensor arrangements that sample nonrepresentatively and are subject to other drawbacks noted earlier.

Although the third major aspect of the invention thus significantly advances the art, nevertheless to optimize enjoyment of its benefits preferably the invention is practiced in conjunction with certain additional features or characteristics. In particular, preferably the current electrodes are roughly equidistant from a centerline or centerpoint of the surface.

An alternative preference is that the current electrodes be arranged in one or more groups, the current electrodes of each group being roughly equal in size and roughly equidistant from a centerline or centerpoint of the surface.

As one such geometry, the ring-shaped current electrodes are arranged in two or more pairs, the electrodes of each pair being roughly equal in size and roughly equidistant from a centerline of the surface. In this arrangement the current electrodes of each pair establish a respective dipole-like electrical field. The sensing electrodes are offset toward each other to locate them substantially at a zero-gradient area of the respective dipole-like electrical field of the corresponding current electrodes.

In another such geometry there are exactly two current electrodes. These are roughly equal in size and roughly equidistant from a centerline of the surface.

Another preference, for this third facet of the invention—if the sensor is for operation in an aqueous medium and susceptible to biofouling—is that the apparatus further include some means for vibrating the sensing-cell surface to reduce or substantially eliminate biofouling of the surface. In this case it is further preferable that the vibrating means be fixed substantially directly to, or substantially integrated into, the surface, ideally at a part of the device that is behind (I.e., in back of) the surface.

Another preference is that the measuring apparatus determine a ratio between a current directed through the cell and a resulting voltage across the cell—or, conversely, between a voltage impressed across the cell and a resulting current through it.

In preferred embodiments of its fourth major independent facet or aspect, the invention is a method of designing a self-cleaning instrument that performs said cleaning by vibration to deter underwater biofouling or chemical deposition. The method includes the step of defining a set of inputs characterizing vibration constraints applicable to generally all such self-cleaning instruments.

Another step is defining an algorithm that generically relates the operating inputs to design specifications of the instruments. Additional steps are receiving a set of values of the inputs for a particular desired instrument; and, based on the values, automatically performing the defined algorithm to compute and provide design-specification values used in designing the particular self-cleaning instrument.

The performing step includes applying at least one of these design principles:

- vibration transmission, from transmitter to critical article to be cleaned, through distance on the order of one centimeter, or less,
- preferably substantially direct attachment of vibration transmitter to critical article to be cleaned,
- preferably substantially unitary construction of vibration transmitter with critical article to be cleaned,
- substantially nodeless vibration in critical areas,
- preferably vibration in order zero or one, and
- duty cycle of five percent or less.

The foregoing may represent a description or definition of the fourth aspect or facet of the invention in its broadest or most general form. Even as couched in these broad terms, however, it can be seen that this facet of the invention importantly advances the art.

In particular, this fourth aspect of the invention expedites design and manufacture of vibratory cleaning systems, and instrumentation integrated with such cleaning systems, that provide the advantages outlined above for the first three facets of the invention.

Although the fourth major aspect of the invention thus significantly advances the art, nevertheless to optimize enjoyment of its benefits preferably the invention is practiced in conjunction with certain additional features or characteristics. In particular, preferably the method also includes the step of designing the instrument generally according to the provided design-specification values.

Another preferable step is building the instrument, as designed generally according to the provided design-specification values. In this case the set of operating parameters preferably includes at least some of these:

- instrument type, and materials of construction;
- geometry, size, weight, and optical and electrical requirements of an instrument, and of its surface or surfaces to be cleaned; and
- environmental conditions under which the instrument will operate.

Another preference is that the set of design specifications include at least some of these:

- vibration-driver type, material of construction, size, geometry, power, and optical details;
- modal frequencies and shapes;
- electronic or other drive-circuit details; and
- a cleaning-performance estimate.

The foregoing principles and advantages of the invention will be more fully understood from the Detailed Description section of this document, with reference to the accompanying drawings—of which:

BRIEF DESCRIPTION OF THE DRAWINGS

FIG. 2 is a longitudinal section (along a centerline) of a variant of the FIG. 1 device, now installed at one end of a waterproof cylindrical enclosure or "can" that also holds related components;

FIG. 2A is a like view, but enlarged, of the portion of FIG. 2 that is enclosed in the line 2A-2A;

DETAILED DESCRIPTION OF PREFERRED EMBODIMENTS

Preferred embodiments of the present invention provide apparatus and technique for enhancing longevity and performance of submerged instruments and many other devices such as those mentioned above. As noted earlier, much of our own interest is in combined sensors for measuring conductivity and temperature in the ocean.

Therefore we focus largely on such apparatus; however, such methods and equipment also serve as examples of the much broader fields in which our invention can be used. Thus the invention is not limited to oceanographic work, or to other systems used in naturally occurring waters, or even to measuring instruments.

Although we are particularly interested in curbing organisms that occur in water, some biological forms occur and can flourish in nonaqueous liquids, and in colloids and gels as well. Reportedly live bacteria have been found in lava flows.

From our initial statement of the field of this invention, it will be clear that biofouling may be associated with fecal matter due to waterborne creatures—or indeed due to land animals including humans. Biofouling, however, is by no means limited to that sort of contamination source.

Thus the invention has broadly applicable capabilities in lakes, rivers and streams, in potable-water reservoirs, tanks, aqueducts and piping, and in industrial chemical-process plants and vats. Our invention is beneficial for virtually every natural and artificial environment in which biofouling or other accumulations of liquid-borne materials (including nonbiological materials) disrupt or degrade equipment operations or biological processes in such liquids.

Thus we ask that the reader consider the following discussion as both (1) specific to the control of biofouling in seawater conductivity and temperature measurement, and (2) exemplary of the restraint of many other disruptive aggregations in liquids.

Embodiments of the invention limit growth of, or in some cases remove, biofouling from sensor surfaces without environmental harm. As noted in the earlier "Background" section, this latter condition is important.

Figure 1:
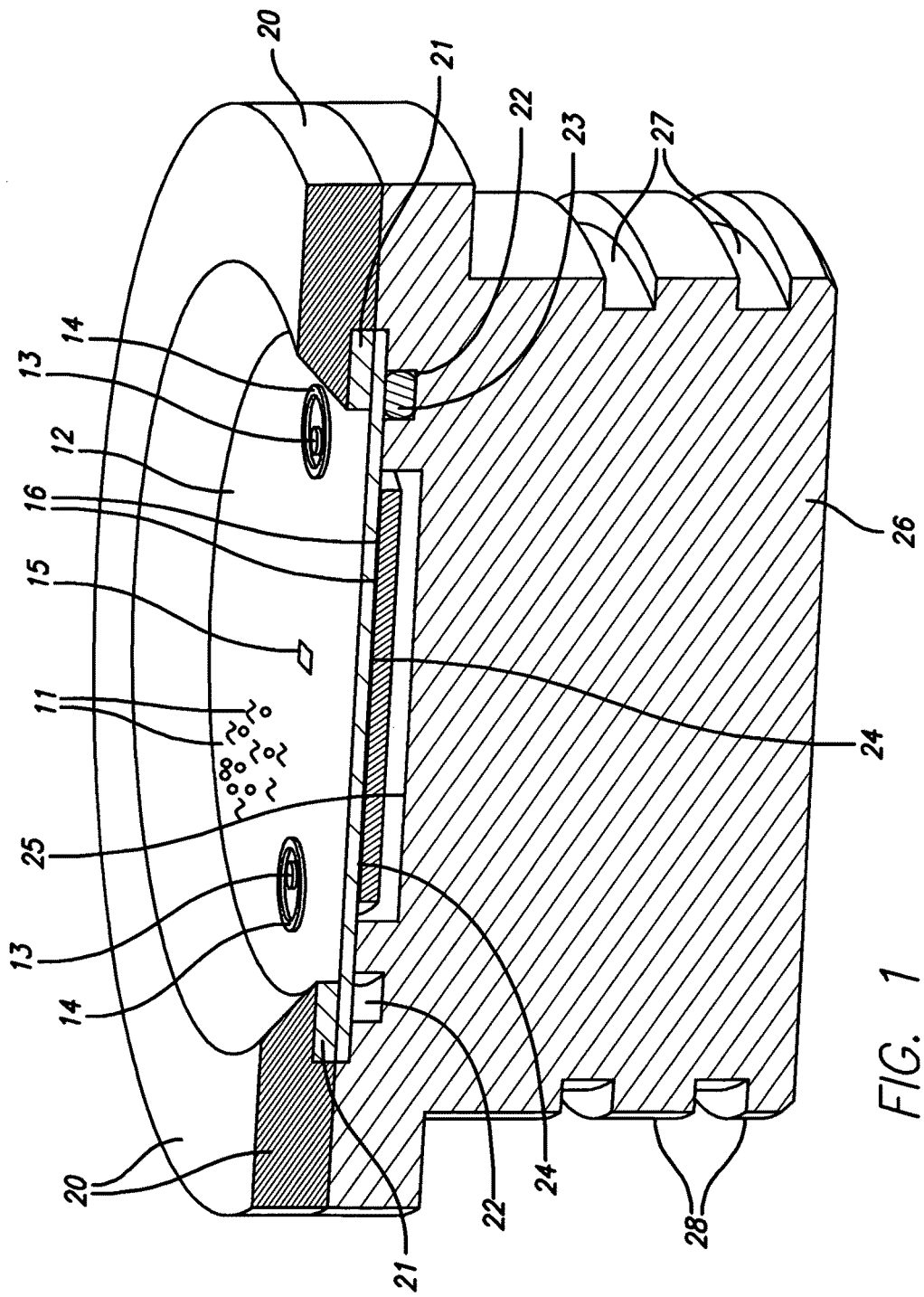
FIG. 1 is a perspective or isometric drawing, partly in longitudinal section (but not along a centerline), of a temperature and conductivity sensor head, including a ceramic disc carrying the sensors—and a representative mechanical vibration driver for cleaning the disc—according to preferred embodiments of the invention.

To achieve this goal, it is usually important to disrupt the so-called "vanguard" of the biofouling cycle: the formation of an initial bacterial layer 11 (FIG. 1). Preferred embodiments of our invention involve incorporation of ultrasonic sources 24, 124 (FIGS. 1 through 3) into sensor platforms 12-15, 20-23—or into other devices such as windows 112 (FIG. 3) with performance-critical surfaces that have correspondingly performance-critical cleaning requirements.

These sources 24, 124 vibrate the critical surfaces 12-14, 112 and their environs at a frequency and amplitude, preferably predetermined, to dislodge those first colonizers of a bacterial film. The size of those organisms has been found to be primarily in the range of 1 to 5 µm.

Figure 16:
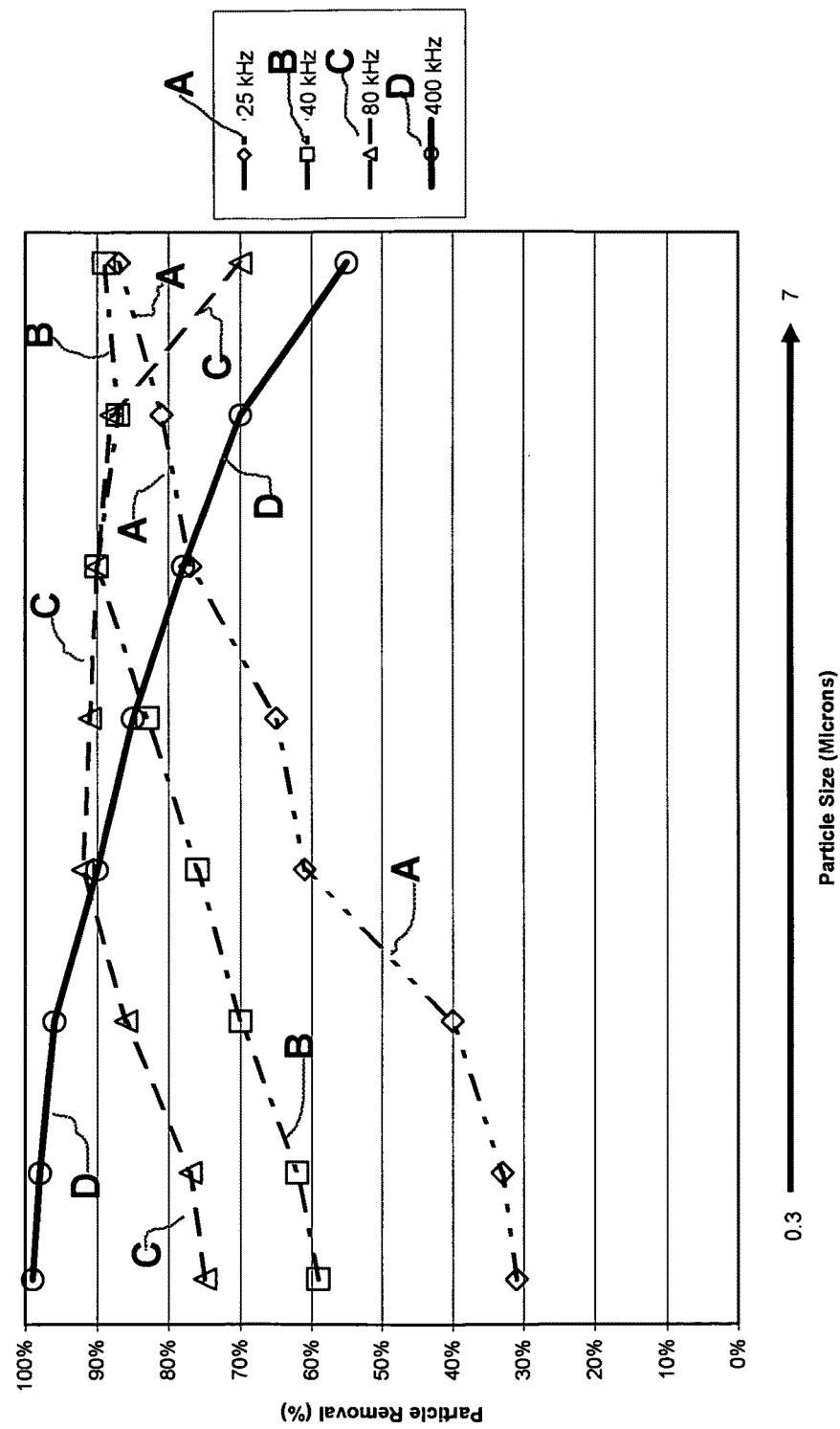
FIG. 16 is a graph of particle-removal efficiency (percentage measure, linearly arrayed along the ordinate) vs. particle size (microns, arrayed along the abscissa on a very roughly logarithmic scale) at various frequencies (represented by four separate curves).

As direct measurements B and C (FIG. 16) make clear, the most effective cleaning frequency for such particles is roughly 70 kHz. We accordingly prefer to use frequencies of that order—but an exception must be noted for measurements D involving relatively small particles, e.g. on the order of one micron. The importance of such direct measurements for any usage of our invention cannot be overemphasized. When particle resonances are used to select or determine vibrational frequencies for cleaning, the vibrational amplitude is determined by the power input into the electronic driving circuit or equivalent driver.

As noted elsewhere in this document, we prefer to operate piezodrivers at approximately fifty or seventy kilohertz to "nearly four hundred" kilohertz—depending on the size and other properties of particles to be removed. To be more specific, one particular frequency that we consider yields good results is three hundred twenty kilohertz. We consider 70 kHz particularly appropriate for particles on the order of 0.1 m diameter; and 320 kHz, for particles on the order of 5 m in diameter—as suggested in FIG. 16. We believe that generally equal quality of cleaning can be obtained using frequencies up to three hundred sixty and even over three hundred seventy-five kilohertz; and perhaps to three hundred ninety kilohertz.

Thus the invention establishes a technique to improve the longevity of oceanographic sensor measurements, one embodiment being temperature and conductivity, as well as many other in-situ sensor applications.

The art of ultrasonic transducers made with thick-film circuit-board fabrication techniques has advanced recently, and now allows development of inexpensive systems of various sizes and form factors. Transducers can be suited to many if not all existing oceanographic sensors and systems, including optical windows.

Some sensors can be cleaned by shaking their ocean-contacting sensor area directly. Others may be cleaned by ultrasonic energy that is transmitted through an associated solid structure 16 such as a mounting plate (with or without adhesive, or mounting gels, etc.).

According to preferred embodiments of our invention, however, in order to be effective such transmission should be through such solid structure over a distance on the order of one centimeter, or less. We believe that this constraint arises through practical, physical requirements for rapid flexure of typical surfaces and structures that make up sensing instruments, windows etc. The energy required to excite the ultrasonic transducers is modest, especially since the duty factor for cleaning can be made minuscule.

According to preferred embodiments of the invention, an ultrasonic cleaning system 24, 16, 124 (FIGS. 1 through 3) is tailored to remove detritus and incipient growth 11 from the critical sensing region 12, 112 of a sensor based on the sensor's physical characteristics. The system is preferably integral to a surface (such as a conductivity cell 12-14 or a window 112) that is critical to the performance of the sensor, and provides a robust and low-cost means of maintaining accurate measurements with a clean sensor.

In addition to cleaning of measuring instruments, other applications including cleaning a vibratory transducer—if its frequency and projected power do not achieve a self-cleaning function. An example is an imaging sonar device, or a projector in such a device. Also included is cleaning the inside of a tube or cylinder.

Frequency and amplitude (and resulting surface acceleration) of the ultrasonic oscillation in the integral cleaning system are best selected to disrupt and dislodge organisms, commonly unicellular, that are the earliest initiators of biofouling. Preferably, the cleaner is to be activated for only a few short intervals each day to disrupt adhesion of these first-arriving organisms.

For these purposes, some aspects of the present invention comprise an ultrasonic oscillator that is mechanically integrated with the surface to be kept clean. Ideally, though not necessarily, the mechanical integration is essentially complete, i.e. the surface is actually unitary with the mechanically vibrating drive element. Such unitary construction appears to optimize amplitude of vibration transferred to the objectionable organisms, though it does introduce some complications (relatively surmountable) in fabrication.

The "Background" section of this document mentions several patents. In regard to the first two of those patents, the present inventors believe that the use of shear (rather than compressional) waves through transmission distances on the order of one centimeter or more, would be ineffective for at least purposes of removing biofouling from sensors and other measuring instruments.

We prefer that the apparatus shake the sensitive surface during nonmeasurement (or other nonoperating) times of the device. This is helpful in some cases, particularly where sensor measurement or other device operation is sensitive to shaking.

Again, one group of preferred embodiments of our invention, a conductivity/temperature sensor 12-15 (FIG. 1) has an intimately attached piezoelectric oscillator 24 to keep the sensor surface 12 clean for extended measurement periods underwater. The ceramic cell 12 is driven at a frequency (~70 kHz) and amplitude consistent with removing bacteria 11 whose size is on the order of 1 to 5 microns. We have tested various prototype sensors, some with piezoelectric vibrators and some without, in a rudimentary simulated oceanic setting.

The conductivity sensor includes two rings 14 and two discs or "dots" 13 and a thermistor 15. In operation current is driven between the two rings 14, and corresponding voltage is sensed across the two discs 13. In another way of operation, the voltage across the discs is set and controlled by a servo, and the current between the rings is measured. In yet another way of operation, the rings and discs are inserted into a measuring circuit in such a way that the apparent impedance of the immersed sensor becomes a circuit element of the measuring circuit.

The piezoelectric oscillator 24 is on the underside of the sensor head 12-15. The head is clamped in place by an annular cover 20, with a compliant gasket 21, between the cover 20 and sensor plate 12—and sealed with an o-ring 23 held in a groove 22. There is an air (or other gas) void 25 under the piezoelectric transducer 24 permits the transducer 24 and sensor plate 12 to oscillate together, very generally like the head of a drum.

Figure 7:
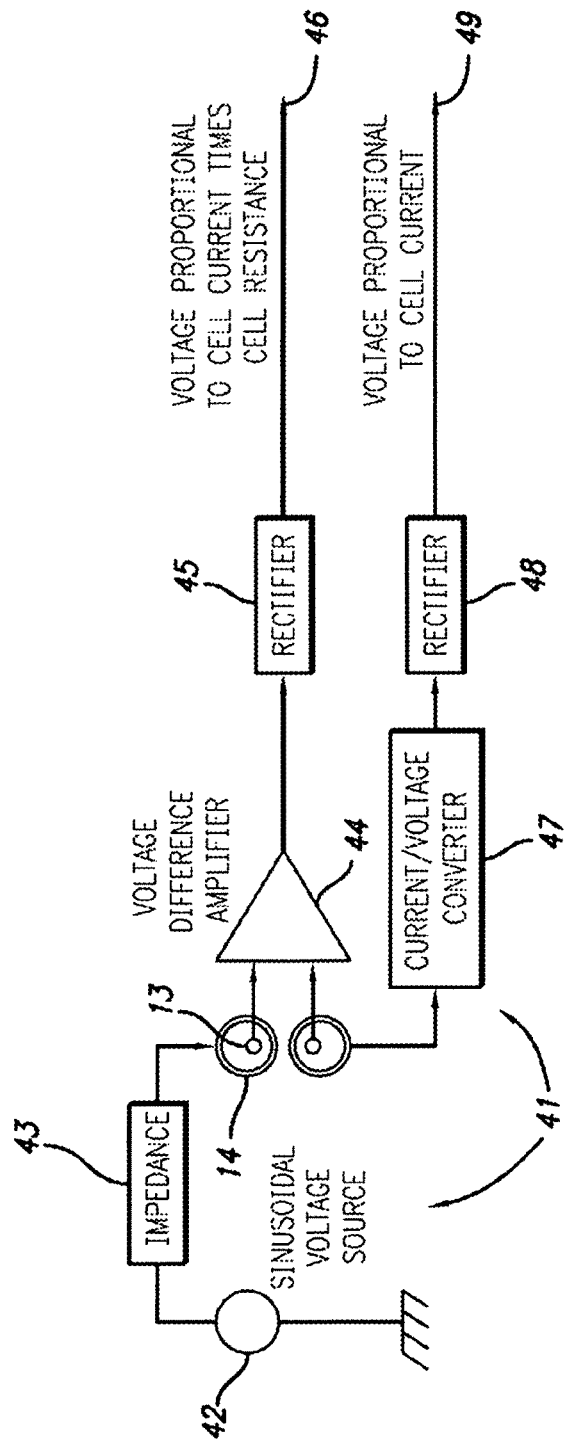
FIG. 7 is a high-level schematic diagram of the FIG. 6 electrodes and an electronic sensing circuit that cooperate to measure conductivity according to preferred embodiments of our invention.

A pressure bulkhead 26 with ribs 28 and grooves 27 for o-rings (not shown) facilitates mounting of the entire sensor head (FIG. 1) into a larger enclosure 31, 26a (FIG. 2) for housing of drive electronics 41 (FIGS. 2 and 7) and feeding of vibrator drive signals 42 to the head and coordinating signals 43 through a connector 32, 33 to and from a computer. The enclosure 31 also houses signal electronics 51, and facilitates feeding of signals 52 to and from the sensor elements 13-15, and sensor output and control signals 53 to and from the computer through the same connector 32, 33.

We have done preliminary modeling of the self-cleaning window and conductivity sensor designs using Finite Element Analysis (FEA) software. As will be seen, the notion of direct flexural modes is throughout our thinking that underlies most or all preferred embodiments of the present invention. The first 50 modes of oscillation were modeled for one of our early conductivity-cell experiments. The study showed the frequencies where the device had the best surface motion without null points. Standing waves of surface motion 12a-12f (FIG. 4) in one modeled sensor were analyzed. As discussed in this document shortly, the interpretation of the analyzed motion is important to design of production embodiments of our invention.

The invention has general applicability to maintaining cleanliness of liquid-immersed instrumentation in both artificial (e.g., process-stream) and natural environments, particularly but by no means necessarily in seawater. Some preferred embodiments of our invention extend the accuracy and longevity of in-situ, temperature-conductivity measurements through integration of an ultrasonic cleaner. A piezoelectric transducer is preferably adapted or customized to suit the size, weight and stiffness specifications of the ceramic-sensor substrate. In our development work, four prototype piezoelectric ultrasonic transducers were mounted behind active and surrogate ceramic conductivity-sensor substrates. The transducers were designed to resonate at a frequency suitable to inhibit attachment of bacteria (particularly in the size range from ~1 to 5 m) to the exposed sensing regions.

For a very preliminary and rudimentary trial, the assemblies were mounted to PVC tubing and submerged in a fish tank. Testing over two separate periods in simulated ocean water indicated that the ultrasonic vibration was effective in reducing biofouling, and in some circumstances chemical deposition (e.g. precipitation of calcium carbonate, or silica originating from algae), on the sensing elements.

Preferred embodiments of our self-cleaning conductivity-temperature sensors enable applications that heretofore have been unfeasible due to access limitations in sensor mounting and maintenance. These applications include longterm deployments on unattended buoys, in food-processing and other process-stream plants, and in water- and sewage-treatment plants. The end-product is an accurate and durable oceanographic temperature and conductivity sensor suite that, as long as the self-cleaning feature operates, does not foul. The self-cleaning feature is useful in a wide variety of fields apart from conductivity and temperature sensing.

Preferred embodiments of our invention further contemplate low-maintenance, temperature and conductivity sensors for use on specific platforms. These enable mutually compatible measurements that yield accurate derived parameters, such as salinity, and advantageously exploit our sensor life-extending technique.

Primary targets for these new devices are longterm, unattended deployments of temperature and conductivity sensors on surface buoys, which are currently of interest to the National Oceanic & Atmospheric Administration (NOAA) and other agencies. Severe problems due to fouling of NAA buoys have been noted for more than a half-century; yet no other worker in this field has introduced straightforward and effective cures such as are set forth in this document. We accordingly believe that our invention is extremely unobvious to people skilled in this field.

In commercial and other applications, sensors can be mounted to the bottoms of ships or other hulls and can measure over extended periods without maintenance. The sensors, furthermore, can be made inexpensive enough to serve as expendable sensors in longterm deployments. Large-area oceanographic surveys using drifters can benefit directly from the longterm accuracy of this technology.

Preferred embodiments of our invention for extending the duration of accurate measurements from these sensors also have commercial applications entirely outside the field of sensor development—and outside seawater measurement applications as well. Food-processing plants, water- and sewage-treatment plants and many others can benefit from using self-cleaning instrumentation, particularly but not limited to sensors.

Piezoelectric ultrasonic transducers can be made in various shapes to match many electrode and sensor configurations. Certain preferred embodiments of our invention have sensors or other device active elements directly on the surfaces of piezoelectric vibrators—so that the vibrator and cleaned device are essentially unitary. While this ideal proximity promises good results, it appears workable to transmit vibrations, through solid links, over somewhat longer vibrator-to-critical-surface distance—up to transmission distance on the order of one centimeter, or less. This concept has value in medical applications as well, where implants and electrodes suffer from protein deposits.

Our work with this invention demonstrates an ability to extend the measurements of needed oceanographic parameters in locations and circumstances historically unavailable due to degradation by fouling. Our piezoelectric transducer cleaning method benefits other sensor technologies also.

Preferred embodiments of our invention successfully overcome the pervasive biofouling problem for the particular case of an oceanographic conductivity and temperature sensor. The sensor is suitable for long-duration use and incorporates a self-cleaning capability into the sensing head.

Temperature/Conductivity Sensor Design:

Temperature and electrical conductivity are among the fundamental parameters that characterize the ocean in three spatial dimensions and time. If these quantities are measured at the same location and in the same temporal and spatial bandwidths they can be combined to derive fundamental seawater properties, including seawater density, sound speed, and salinity. The open-ocean density and salinity parameters derived from frequently sampled temperature and conductivity data (as detailed in Woody, et. al., "Measurements of Salinity in the Coastal Ocean: A Review of Requirements and Technologies," *ITS Journal* 34 No. 2) are necessary to understanding of global climate, hydrological cycles and circulation, and biological environments. In coastal waters, salinity measurement is important to understanding of ecosystem functions such as spread and potency of pathogens, sustainability of nursery areas, and algal blooms. Longterm measurement of coastal salinity also aids in the understanding of physical processes such as freshwater runoff, estuarine mixing, and coastal currents.

We have developed many paired conductivity and temperature sensors over the last twenty years. These systems have been and are still used, e.g. in tactical oceanography and oceanographic R&D. They have been deployed with in-situ periods ranging from long on platforms to short as expendables. Thermistors have usually been used to sense temperature; conductivity has been measured using water-contacting cells made with noble metal applied as thick-film inks that are applied directly to ceramic and fired. These techniques give the sensor designer latitude for size, shape, and functionality of each sensor. The sensors meet stringent requirements, such as bandwidths to tens or hundreds of hertz and spectral sensitivities to only a few microkelvins and a few hundred nanosiemens per meter per root hertz. By building on our previous techniques, we have developed a simple temperature sensor and a unique planar electrode conductivity sensor that meet fine accuracy and nonfouling criteria.

One end-product of preferred conductivity/temperature sensor embodiments is a low-cost, robust sensor employing a unique combination of conductivity sensor, temperature sensor, and embedded ultrasonic cleaning device that removes detritus and incipient growth from the sensor head(s). Temperature and conductivity measurements are programmable for intervals varying from continuous to sparse in order to conserve power and to suit application requirements. The frequency and amplitude (and resulting surface acceleration) of ultrasonic oscillation in the integral cleaner are selected to disrupt and dislodge the smallest unicellular organisms that are at the vanguard of biofouling. The cleaner is activated for only a few short intervals each day to disrupt early adhesions of fouling organisms. For protracted periods, the clean sensor surfaces promote specified sensor accuracy without requiring recalibration due to biological infestation.

The conductivity/temperature sensor embodiment includes, within a single ceramic substrate, collocated measurements of temperature and electrical conductivity, with an embedded piezoelectric oscillator to eliminate biofouling. One preferred embodiment of the sensor system comprises:

a thick-film, planar, four-electrode conductivity sensor;
an embedded or attached, preferably integral thermistor;
a preferably integral piezoelectric transducer for sensor cleaning;
sensor circuitry for the temperature and conductivity sensors;
drive circuitry for the ultrasonic cleaner;
digital timing, acquisition, and data-transmission circuitry;
power-management circuitry; and
a pressure vessel for enclosing the circuitry—and with mounting hardware, and connectors through the vessel walls.

The ceramic substrate is mounted on the electronics package with the sensing elements exposed to the seawater or other liquid. The inner surface of the ceramic element faces a void within the pressure vessel, and electrical connections for the sensors and the ultrasonic source are attached. The ultrasonic source is either integral with the ceramic laminate or coupled to it in such a way that the two do not separate during vibrational cleaning of the sensors. The pressure-proof packaging is simple and inexpensive, commensurate with the low-pressure requirements of the application.

Preferred embodiments of this invention increase the duration of accurate measurements with a new generation of self-cleaning temperature/conductivity sensors that are useful in many oceanographic scenarios from moored to towed applications—and also in freshwater, biological, medical, and food-processing applications.

A sensor according to preferred embodiments of the invention measures water temperature and conductivity simultaneously and at the same location with sufficient accuracy to support the determination of salinity to within 0.1 practical salinity unit (psu) and better—not markedly better than performance exhibited by some of our early developments. This present sensor, however, is designed to keep its own measuring surfaces free from detritus and fouling, supporting unattended accurate measurements for protracted periods, e.g. a year or more.

An objective of our invention is that its detailed interfacing onto an actual field platform or a test platform requires only information about power, data-acquisition and storage interfaces of the platform. Given that those specifications are accommodated, the final interfacing design can be completed.

Thermistors suitable for use in our invention come in a wide variety of resistance scales and mechanical forms, and are relatively inexpensive and easily employed to withstand the rigors of oceanic use. For many applications, preferred embodiments of our invention utilize laser-trimmed thermistor elements in chip form that are ready to apply directly to a circuit board by automated means. These thermistors are insulated from the ocean water, preferably by the use of a conformal coating such as e.g. Parylene, which we have tested. In some situations such coating may be applied over an entire circuit board to which the thermistor is mounted.

For geometries that are closer to our temperature/conductivity sensors, the thermistor can be instead mounted to a circuit board that is behind a generally planar-faced ceramic disc. The disc face carries conductivity-sensing electrodes and has an orifice for the thermistor. The thermistor extends partway through the disc, with its end slightly recessed in the face. The conformal coating is applied over only the thermistor, just filling the recess so that the face, including the coating, is flat.

Although in the abstract such relatively extreme flatness can be beneficial, as a practical matter this attachment method would make fabrication of the ceramic circuit board difficult. In one of our preferred embodiments accordingly a chip thermistor is mounted directly to the planar-faced disc. The disc face carries conductivity-sensing electrodes as described above, but also has soldering positions—located between the conductivity electrode pairs—for the thermistor. In its mounted location, the thermistor extends above the surface of the disc. The conformal coating is then applied over only the thermistor and its corresponding solder connections, thus insulating it from the conducting ocean water.

Our new technique thus presents to the water an acceptably flat sensing surface which is inherently easy to clean and does not harbor macroorganisms. The planar conductivity cell preferably employs a novel electrode pattern to enhance measurement accuracy, which is historically problematic with open-face cell geometries. The electronics for the conductivity cell preferably use an innovative technique that simplifies the circuitry without sacrificing accuracy, and can also eliminate the need for platinizing the sensor head to reduce the interfacial contact impedance. Electronics for the temperature sensor preferably apply a resolution-enhancing approach.

Preferred conductivity sensors of the present invention, apart from the novel self-cleaning features that very greatly extend their useful accurate life, are related to sensors using thick-film screening techniques that we developed previously. Development of these sensors started in the mid 1980s and went forward as reflected in our patent documents and our other publications listed later in this document. Those earlier developments were not optimized for longterm absolute accuracy, as sensitivity, bandwidth and survivability were more important. We used an open-cell geometry for these embodiments to reduce clogging or occluding the sensor, which is prevalent in sensor types that employ closed-cell geometries. We have, as in the embodiment described earlier, included modifications to our standard open-face cell geometries to enhance longterm stability.

Conductivity Cell Design:

Preferred embodiments of the conductivity sensor in the present invention include a planar cell, with its electrodes positioned to enhance accuracy. Our previous goal, in our earlier work, of centimeter-scale spatial resolution is now greatly deemphasized. Like-wise, our early sensors' requirements for sensitivity to microkelvin and nanosiemen-per-centimeter fluctuations at high bandwidths are not pursued. Instead, approaches that increase absolute accuracy, developed in more-recent programs, are carried through, and when possible enhanced. One preferred approach to increasing the absolute accuracy of planar conductivity cells is to increase the scale of the electrodes. Another preferred approach is to position the voltage-sensing electrodes that are situated within the current drive rings in such a way that they are located at zero-gradient points in the field generated by the current drive rings.

Increasing the dimensions of the planar conductivity cells is the easiest part of the approach to increase absolute accuracy. A second preferred modification is to position the voltage-sensing electrodes, which are situated within the current-drive-ring electrodes, in such a way that they are located at zero-gradient points in the electric field generated by the current-drive rings. Conductivity measurements are least sensitive to small dimensional perturbations (due to, say, cell erosion or surface contaminants) when the sensing electrodes are at such points.

We have studied the electric fields generated by our isopotential planar ring-electrode patterns. We determined the electrical field of the drive rings as a function of ring diameters and their separation. The positions of zero gradient are located slightly closer to the centerline of the sensor than are the centers of the drive rings. In our preferred geometries discussed in this document such positioning provides better d.c. stability of planar cells, and such cells are better for self-cleaning instruments as they do not protrude.

Figure 6:
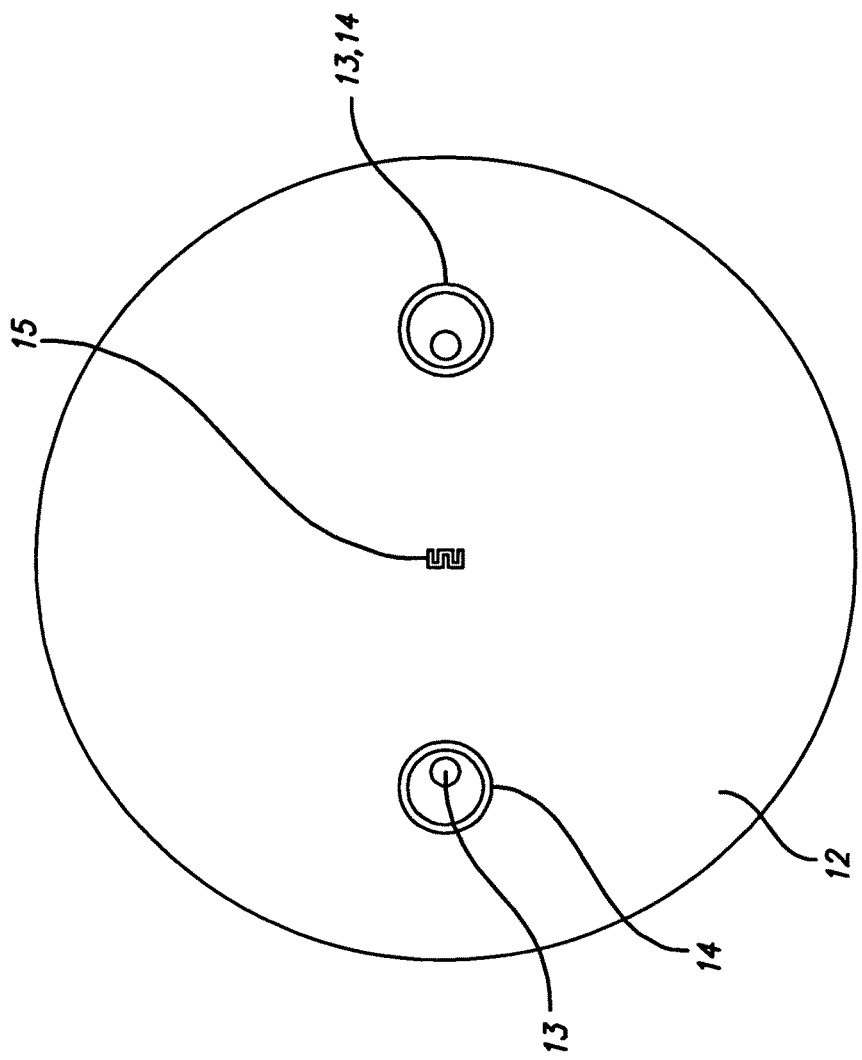
FIG. 6 is a top plan view of the FIG. 1 sensor disc showing (as does FIG. 1) a temperature sensor and conductivity sensing electrodes in one of many line-symmetrical geometries usable for purposes of our invention.

We have designed a preferred planar conductivity cell according to the principles of the invention as set forth herein, and fabricated the thick-film sensor to our specifications. The electrode patterns 13, 14 (FIG. 6) are fabricated using platinum/gold thick-film ink screened on the surface of a 2-inch diameter by 0.045-inch thick thick-film LTCC (low-temperature, cofired ceramic) circuit board 12. In one form of this device a current is forced into the water between the ring electrodes 14, thereby establishing a corresponding voltage across the gap between the disc (or "dot") electrodes 13, within the respective rings 14. The voltage is then monitored to complete determination of the conductance as the current-to-voltage ratio.

For other possible systems, as will be understood the general object remains the sensing of conductance or impedance—and this can be accomplished either as described above or in a converse manner, i.e. by impressing a voltage between the disc electrodes and monitoring the resulting current between the rings. Yet another approach is to design an external measuring circuit (not shown)—for connection to the electrodes 13, 14—which causes the impedance of the cell to become a circuit element of an external measuring circuit. The cell impedance is then measured by that circuit.

The voltage-electrode discs 13 (FIG. 6) are displaced inward from the centers of the respective current-electrode rings 14, in order to locate the discs 13 at a zero-gradient area of the dipole-like electrical field of the rings. This configuration represents a family of designs that has line symmetry; thus another member of the "family" would have additional ring-and-disc pairs of electrodes (not shown) arranged at positions stepped perpendicular to the axis of the pattern. Any geometries in this family maintain their internal relationships if the configurations are imagined to be "folded" along a line of symmetry down the center of the pattern.

Figure 6A:
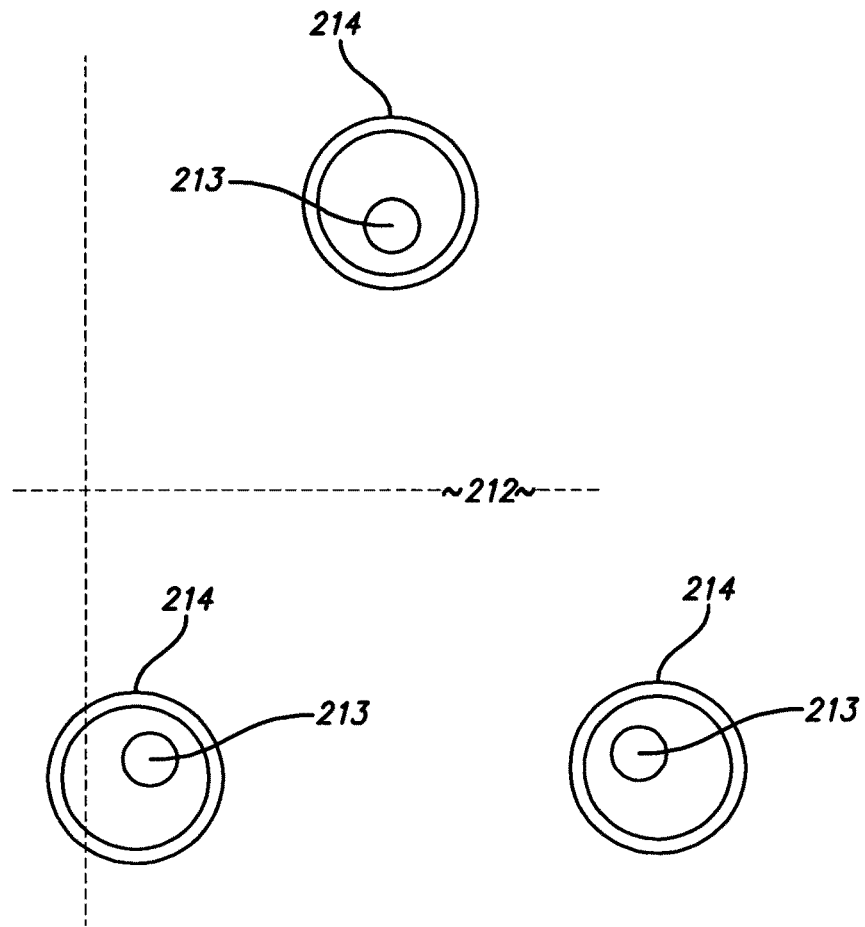
FIG. 6A is a like view but of only the sensing electrodes, and in one of many point-symmetrical geometries usable for the invention.

In an alternative family of designs, an analogous related configuration instead places the rings and discs 214, 213 (FIG. 6A) in a family of configurations that has point symmetry. Here the discs 213 are still displaced inward from the centers of the respective rings 214—but here the relationships are maintained if the configurations are imagined to be "rotated" about a point of symmetry at the center of the pattern. This geometry is suited for, e.g., a three-phase drive.

The diameters of the prototype sensors were designed to best accommodate the piezoelectric transducers that provided the self-cleaning feature. Conductivity sensors were made with and without piezoelectric elements. We also made dummy prototypes, with the same shape and mechanical properties as the active substrates but no active piezoelectric elements. Fouling comparisons were later made using conductivity sensors with and without active piezoelectric elements.

Conductivity Circuit Design:

The electronics design in preferred embodiments of our invention is significantly different in approach from many established conductivity sensor designs (including our own earlier designs). One major difference was motivated by the use of ultrasonic cleaning: platinization in conventional conductivity-measuring cells has been discussed earlier in this document. In the development of this sensor, we realized that if platinization were used, it might be dislodged by the repeated cleaning cycles effected by the piezoelectric transducers.

Therefore, preferred embodiments of our invention use a conductivity sensor drive frequency at which the measurement is not improved by platinization—and accordingly do not use platinization. The frequency of the a.c. current that is driven through the water is, very roughly speaking, 100 kHz. At this frequency, the current into the water is predominantly carried into the water by capacitance, rather than by the resistive component of the electrode-water interface.

The conductivity sensor must make precise measurements to support derivation of the oceanographic parameters of interest. Our design requires operational amplifiers that can be used in precision circuits at operating frequencies of 100 kHz. Such amplifiers have recently become available.

Our preferred design measures conductivity by forming the ratio of an imprecise current and a corresponding voltage in the water. Most systems use precision currents, but our preferred embodiment instead measures an imprecise current precisely. To be more specific, the ratio of the cell current—between the ring electrodes 14 (FIGS. 1 and 6)—to the corresponding voltage (between the current disc or "dot" electrodes 13) is the apparent conductance in the planar conductivity cell. Precise ratiometric digitizers have been routinely available for some years, and are well-suited for determining the needed ratio.

As mentioned earlier, such a ratio can be found in various ways. A current can be driven between the rings, and both the current and the resulting voltage between the discs measured—and the ratio found from those measurements.

Instead a voltage can be impressed across the discs, and both that voltage and resulting current between the rings measured—and the ratio found from these measurements. Still other measurement strategies for sensing the effective impedance itself are available and described elsewhere in this document.

As to the electronic circuitry for our conductivity sensor, a 100 kHz sinusoidal oscillator 42 (FIG. 7) produces a 4 V peak-to-peak drive. That voltage is in series with a relatively large impedance and the conductivity-cell current rings 14, and in one of the strategies already outlined above drives current through the seawater. The resistance across the conductivity cell 13, 14 is only a few tens of ohms, varying with conductivity of the water that is in contact with the cell.

The cell current flows into a current-to-voltage converter 47, whose input impedance is effectively zero ohms by virtue of its feedback design (not shown). Current through the conductivity cell 13, 14 is about 1 mA (a safe, low value for electrodes of the size used). This cell current is measured by the current-to-voltage converter 47 and then rectified 48 to produce a precise output 49 that is a measure of the magnitude of the drive current through the rings 14.

A difference amplifier 44 measures voltage generated between the receiving disc electrodes 13, due to the 100 kHz current that is driven through the ring electrodes 14. This signal from the voltage-measuring disc electrodes is also sent to a rectifier 45, which precisely determines its magnitude 46.

Thus both voltages are converted to d.c. levels by the rectifiers. The ratio of the outputs of the two rectifiers 45, 48 reveals the conductivity of the water. This ratio is proportional to cell resistivity or cell conductivity, depending on which output voltage 46, 49 is put into the numerator.

In practice, in preferred embodiments of our invention the circuit directly calculates the resistivity of the water, and the reciprocal of that value is presented as the conductivity. We prefer to make the resistivity the directly computed variable because ratiometric digitizers are more precise if operated with nominal and nearly constant reference (i.e. denominator) voltages, and the cell current remains nearly constant over substantial changes in water conductivity. The circuit operates from plus-and-minus 5 V supplies, and draws 50 mA from each supply.

Temperature Sensor Design:

Our preferred temperature-sensor approach uses a version of the standard series connection of a resistor and the thermistor. An inexpensive d.c. voltage reference drives the thermistor and resistor, and provides the reference voltage for one of the same kind of digitizer that the conductivity sensor uses. We do not use the classical zero-curvature-at-midpoint resistance-to-temperature calibration technique. We have developed a preferred approach for the thermistor's series resistor selection and a calculation technique that reduce computed errors to a few millidegrees across the full scale. The digitized output is reduced to temperature by a polynomial algorithm.

In our initial development, the thermistor was not integrated with the self-cleaning sensor head; now, however, in practice of the invention we prefer to place a small, monolithic thermistor 15 on the surface of the ceramic sensor plate 12. Temperature-equilibration delays at the thermistor are not a problem since the measurement bandwidth requirements are very low.

In a thorough analysis of the thermistor circuit, we confirm that the circuit is capable of better than 5 m° C. resolution. In one laboratory test, with a decade box substituted for a thermistor; we find that the digitizer circuit can provide 3 m° C. resolution.

The resulting design supports all measurement accuracy requirements in the application, and easily interfaces with the conductivity measurement circuitry.

Piezoelectric Transducer Design:

In one preferred embodiment of our invention, the self-cleaning feature of the sensor system is implemented with an ultrasonic piezoelectric transducer attached to the back of the ceramic sensor. A thick-disc ceramic transducer is cemented to the sensor head. For this application the transducer is designed to shake the entire active sensor area in a nodeless fashion. Vibration at 70 kHz is preferred for, specifically, best control of most organisms in the earliest stages of biofouling.

For other applications or embodiments, ideal vibration is typically in a drumhead mode, e.g. zero-order or first-order—or in a higher-order mode that has no nodes in the region to be cleaned. In general the objective is to select a vibrational mode that cleans to a design level of cleanliness for the performance of the device. An electric field across the two faces of the transducer drives the ultrasonic vibration.

Ultrasonic flexing prevents adherence of detritus and the attachment of bacteria on and in the neighborhood of the conductivity electrodes. Preferably the ultrasonic flexing is activated periodically, with a period that is short enough to remove detritus and at a time when microorganisms have not yet had time to become well attached. The biological and chemical processes for firm attachment of fouling require times that are much longer than the interval between periods of ultrasonic excitation. In these short intervals, the contaminants adhere weakly, and amplitude of vibration that dislodges the contaminants does not also disrupt the metal-to-ceramic bond of the conductivity electrodes to the face of the sensor.

The amplitude of ultrasonic vibration that removes weakly attached detritus and bacteria may, however, also remove black platinization from a conductivity cell. The black platinization adheres very weakly, as was mentioned in the description of the design of the sensor. The high-frequency conductivity sensor operates at a high enough frequency that the black platinum is not needed to maintain sufficiently low contact impedance, and therefore we refrain from applying it.

A very generally representative ultrasonic transducer (actually one that we used in an early experiment) is a piezoelectrically active ceramic disc 24 (FIG. 8) with perforations 45 for sensor leads to pass through to connection pads 44. When a positive voltage is applied to one face 24 of the transducer (as e.g. from the position of a mounting plate or adhesive 16, FIG. 1), and a negative voltage to the opposite face 24, the disc flexes toward the positive-voltage side. In this experimental unit, transducer-actuating voltage was applied to the visible side 24 of the disc through metal tabs 54.

When such a transducer 24 is fixed to a conductivity-cell disc 12 (FIG. 8)—which in preferred embodiments of our invention is typically or preferably also ceramic—that disc 12 deflects too, because the two ceramic pieces are bonded together. The transducer 24 is fixed to the "back" of the sensor disc 12—i.e., to a face of that disc which does not contact water.

In order to effect the shaking motion that keeps the face of the sensor clean, an a.c. electric field at the mechanical resonant frequency is applied between the two transducer electrodes, causing the entire unit to shake back and forth in the manner of a drumhead (i.e., as illustrated, in and out of the plane of the paper). For best cleaning the vibrator should be designed to operate in a mode with minimal "nodes", i.e., "nulls" in areas of the surface which are critical to good performance of the sensor (or other device to be cleaned). Although high-order modes can be used if they provide essentially nodeless operation in such critical areas, it may be easiest to conceptualize the invention—and in some cases easiest to implement it—with modes of order zero or one.

Figure 5:
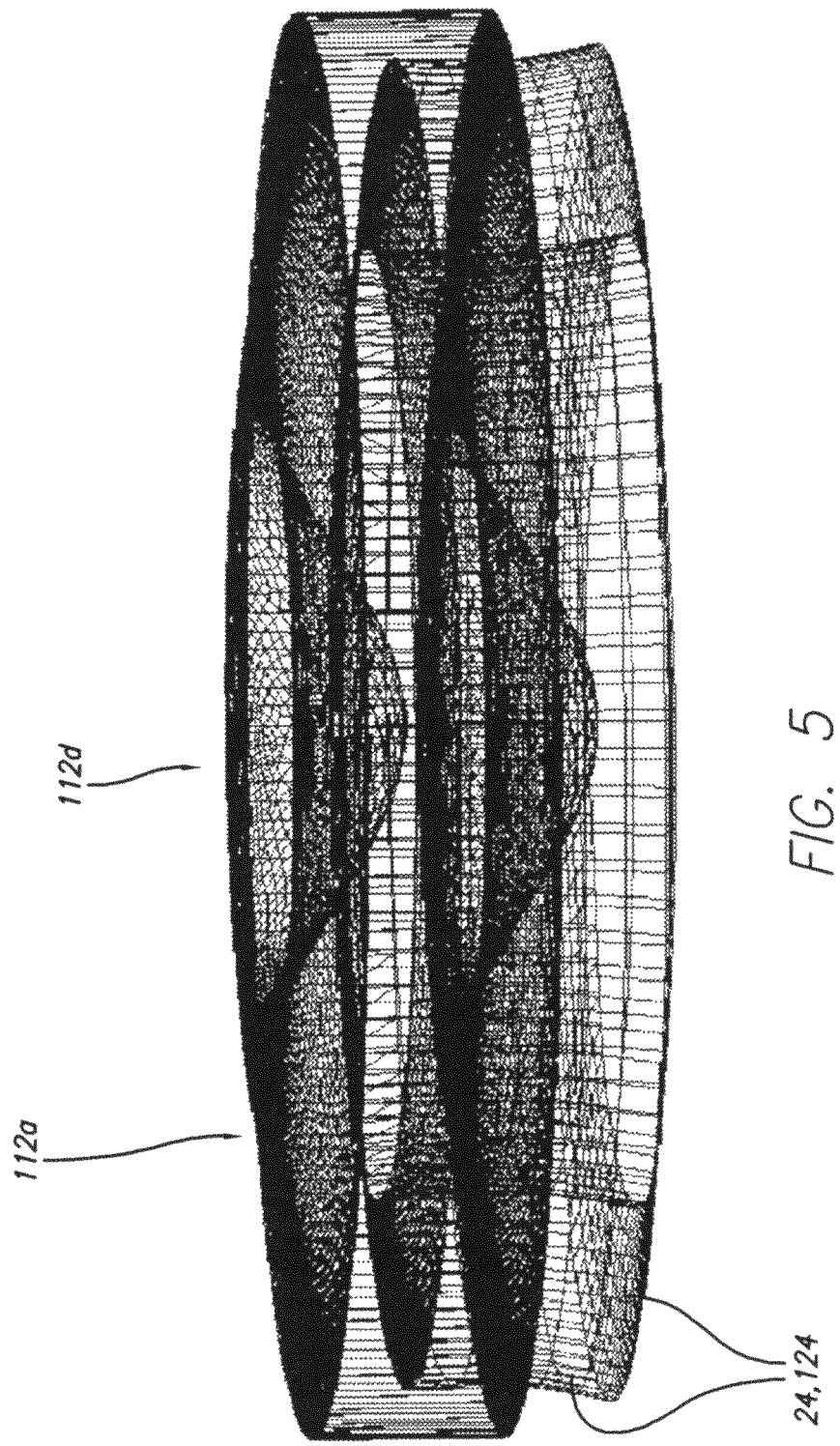
FIG. 5 is a like view of such a disc-shaped element together with a vibration transmitter or mechanical vibration driver shown inducing vibration in the disc.

Nomenclature as to identifying vibrational modes varies somewhat in this field and related fields. Zero-order, as some people skilled in this field use the term, corresponds to bodily movement of an entire disc, without flexing, in the direction stated above. First-order, sometimes called a fundamental mode, corresponds to maximum motion at only the disc center 112*d* (FIG. 5), while the edge remains stationary since the disc is rigidly fixed there.

Figure 4:
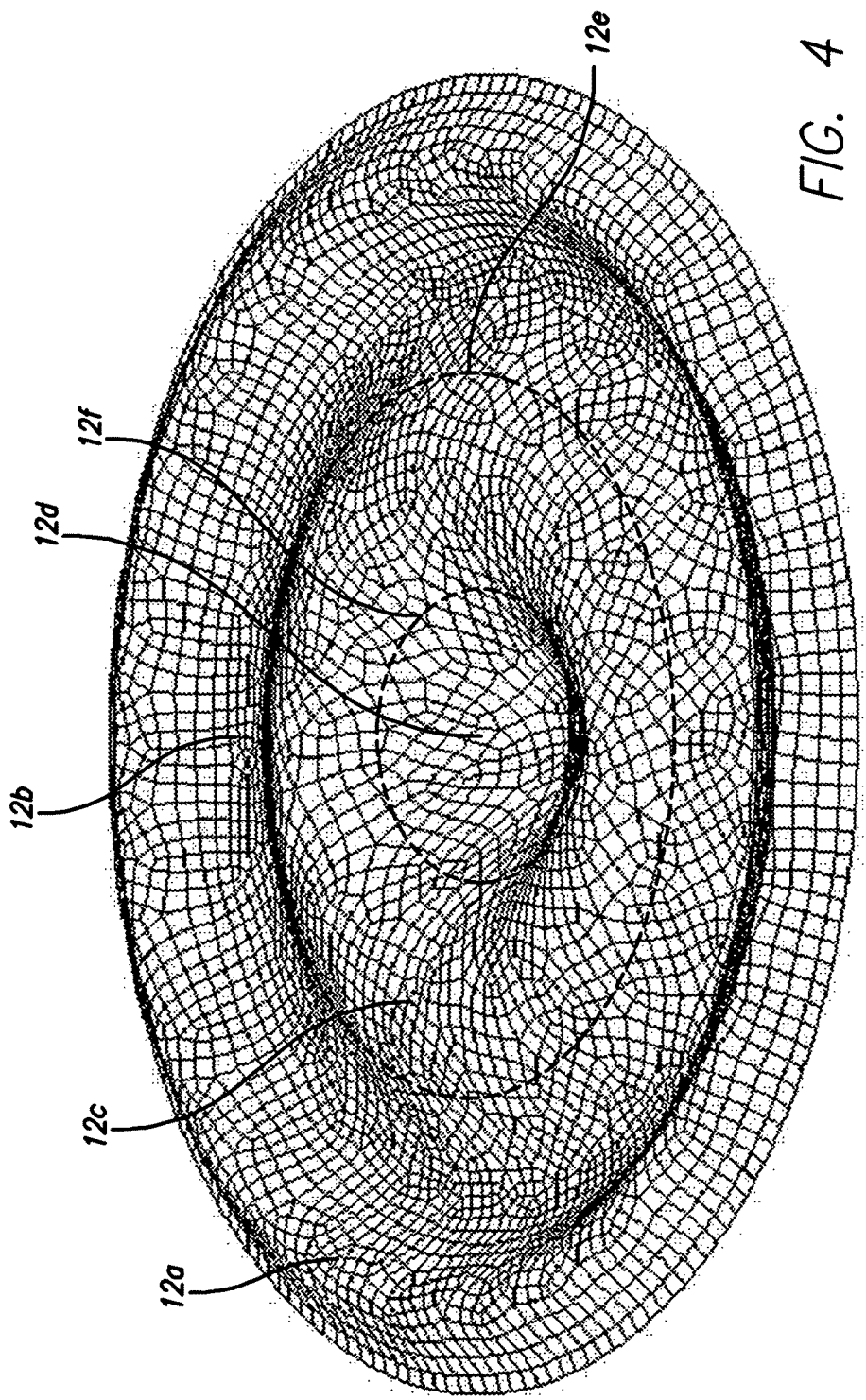
FIG. 4 is a perspective or isometric wire-grid drawing, prepared by a computer-aided design program and with vertical dimension very greatly exaggerated, of a vibrational mode that can be induced in e.g. the FIG. 1 ceramic sensor disc, the FIG. 3 disc-shaped window, or other circular element—according to some embodiments of our invention.

A typical higher-order vibrational mode has plural troughs 12*b*, 12*d* (FIG. 4)—and between them ridges or peaks 12*a*, 12*c* (FIG. 4). Between the peaks and troughs are typically nodes or "nulls" 12*e*, 12*f* that may propagate about the surface but more commonly are stationary with respect to it, i.e. are parts of a so-called "standing wave" in the surface.

Subject to details of amplitude etc., such standing nodes in critical areas of the surface to be cleaned are to be avoided, since in essence the surface is not moving at the nodes. All of this behavior must be studied with care for each different combination of disc geometry, materials, operating conditions etc., as other vibrational characteristics can become quite important.

Barring such complications, a broader area 112*d* (FIG. 5) of effective cleaning near the center of a sensor disc 12, 112 may be achieved by operating the vibrational driver 24, 124 to establish a fundamental mode. No movement is provided around the edge, and only modest movement at positions 112*a*, partway out from edge to center; but this can be effective if the critical surface to be cleaned is only near the center.

By way of summary and review: a disc-shaped surface may be driven as one unitary element (often called a "zero order" mode) rather than in a deforming fundamental or harmonic mode that leaves some regions unmoving. Alternatively, and in some cases we believe more easily, the surface may be driven in a fundamental or low-harmonic mode that vibrates an entire region where the actual sensing occurs.

Apart from the matter of node selection, and all other things being equal, greater shaking is achieved by driving the transducer with a higher voltage at a resonant frequency. Power required, however, is proportional to the square of the applied voltage; hence in practice of our invention it is advisable to experimentally determine trade-offs between electrical power usage and cleaning efficacy. In accordance with our invention we prefer to drive an ultrasonic source harder for shorter times to achieve the best cleaning per amount of energy used.

At strong drives, the cleaning duty factor may be on the order of 0.1%, or only a few minutes spread across each day. With such a strategy it becomes very easy to select sensor-operating times that are not disrupted by operation of the ultrasonic cleaner.

Cleaning requirements for this application are relatively undemanding—i.e., by virtue of better coupling and the associated more-direct shaking, the system enjoys lower power requirements. The objective is met more easily than in most ultrasonic cleaning applications because only the cleaner itself and its immediate environment need be cleaned.

Early Experimentation—Saltwater Test Bath:

Our test sensor head was designed to resonate at approximately 70 kHz. We chose this frequency based on the particle sizes (1 to 5 microns) that we wanted to inhibit from attachment to the sensor face. We measured the resonant frequency of the sensor-transducer assembly: it was 70.2 kHz, i.e. quite close to our design specification. The drive voltage on the ultrasonic transducer was at a relatively low value of 10 V in our early testing work, compared with values on the order of 30 V, which we now prefer for routine practice of present prototypes of our invention. In the latter environment, cleaning forces are correspondingly higher as well. (It must be recognized, however, that such values are not fully representative of all models or usages of the invention—applying only to the specific geometries, materials and other variables involved.) We now believe that a most-useful range of drive voltages extends, with associated adjustment of related parameters, between very roughly 10 and 100 V.

The entire test package was mounted in a saltwater tank. The tank water was inoculated with organisms such as *Nitromonas* and *Nitrobacter*, to maintain acceptable ammonia and nitrate levels, and a plethora of microphytoplankton. The environment was moderately well controlled: a heater maintained a constant temperature of 25 to 26° C., and natural sunlight was augmented by a 60 W so-called "grow light". The water quality was monitored and a log of temperature, conductivity, pH, ammonia, nitrates and nitrites was maintained. Growth of bacterial film in the tank and on each assembly was monitored daily.

In these very preliminary lab sensor-vibration tests, we found that some species of waterborne contaminants were deterred from deposition on sensor surfaces—or were partially removed, after deposition, from sensor surfaces. A more interesting and potentially even more useful finding, however, was that after the vibration our sensor surfaces exhibited a geometrical pattern of remaining deposits, evidently corresponding to vibrational nodes and maxima as discussed above. More specifically, residual deposits were heavier along nodal lines and regions, and lighter along vibration-maxima lines and regions.

In general our objective is to remove or deter all deposits, rather than only those at highly localized vibration maxima. Therefore, as already observed in the preceding section of this document, a noteworthy conclusion from our testing is that the vibration driver and geometry of the sensor surfaces, and their interconnection, are ideally designed to minimize nodes—since biodeposition at nodes cannot be very effectively deterred or removed.

Figure 9:
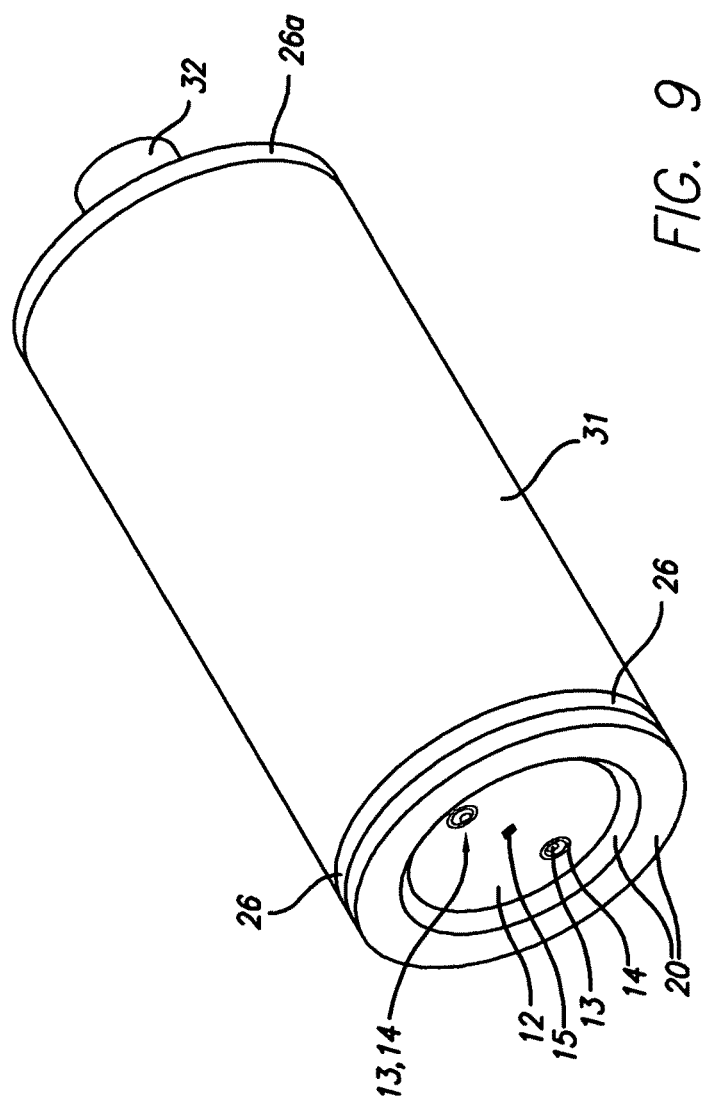
FIG. 9 is an external isometric view of the FIG. 2 can, taken looking at an angle toward the sensor-head end of the assembly.

Design Considerations:

Given the teachings of our invention, mechanical design can straightforwardly implement those teachings. In preferred embodiments the sensor electrodes 13-15 (FIGS. 1, 6 and 9), ultrasonic transducer or driver 24 (with adjacent oscillation chamber 25), seals 21, 23, and electronic connections 42, 52 (FIG. 2) are mounted to the sensing head 12. Ideally the system also includes a pressure vessel 31 (FIGS. 2 and 9)—essentially a shell to enclose electronics 41, 51 and other sensitive components, and keep liquid out.

In one preferred such design, as mentioned earlier, the ceramic sensor head or substrate 12 is mounted between a rubber gasket 21 at the front of the substrate and an o-ring seal 23 at the back—i.e. inside the vessel. This mounting design allows the piezoelectric transducer 24 and sensor disc 12 to oscillate separately from the mounting 20, 26—i.e. in a mode sometimes called "zero order"—thereby greatly increasing the sensor-head 12 displacement, substantially everywhere on the disc, relative to that in our preliminary experiments described above.

We also favor this geometry for its tendency to reduce the stiffness of the overall assembly. For shallow-water applications the sensor-head mounting and the pressure vessel are preferably constructed of engineering plastic. We now prefer materials such as Delrin and Ultem, either with or without glass reinforcement. In the preferred form of the sensor the shell 31 (FIGS. 2 and 9) is cylindrical housing, of dimensions suited to the sensor 12-15 and to the electronics and other components that it is to contain—and also to any mechanical constraints imposed by the environment.

Thus the dimensions may be quite small or quite large, as appropriate. In purest principle we now see no reason to exclude shell dimensions on the order of, e.g., millimeters; or on the order of e.g. many meters. For instance the shell may actually be an underwater station (e.g. a staffed or unstaffed station) or underwater craft.

In one representative prototype that we designed, this cylinder was roughly three inches in diameter by six inches long; however, it should be noted that these dimensions were essentially arbitrary, and what counts is suitability to the operating environment and desired contents. As to application for oceanographic measurements, such a sensor is small enough to be mounted in any one of various locations on virtually any measurement buoy or other platform. Preferred embodiments of our invention, as now known and practiced, cannot yet clean window areas, and the like, up to four inches square; however, we believe that with continuing development work the invention will be readily able to handle surfaces of that size and larger. Therefore such surfaces are deemed to be encompassed within certain of the appended claims.

As mentioned elsewhere in this document, our invention preferably transmits vibration through surface-to-surface distance on the order of one centimeter, or less—and even that through a substantially solid medium. More preferably, however, the vibration is transferred directly from the vibratory driver to the critical element (window, sensor disc, etc.) by essentially direct attachment; and most preferably the driver and the critical element are fabricated as (or fabricated to form) one unitary component.

In some of our ocean-sensing designs, a chip thermistor 15 (FIGS. 1, 6 and 9) is placed between the conductivity electrode pairs 13, 14. It is waterproofed by coating it with Parylene, which does not extend to the conductivity-electrode areas. We have tested this use of Parylene and find that the coating accomplishes the sealing task without adversely affecting the frequency response of the temperature measurement. (Further details of applying the coating appear elsewhere in this document.)

Figure 10:
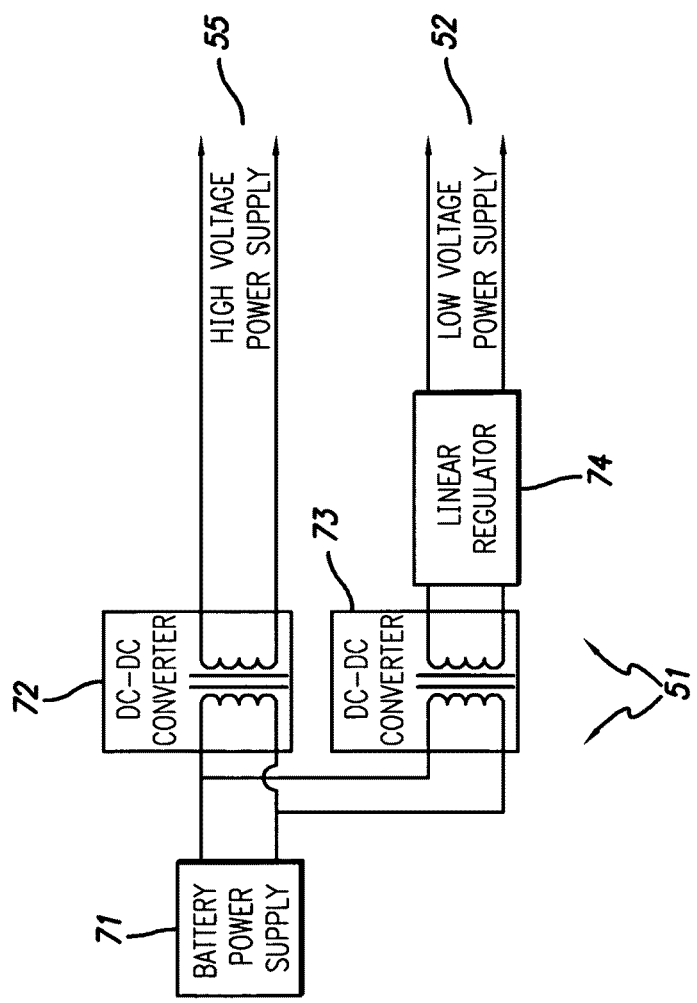
FIG. 10 is a view like FIG. 7 but showing representative power supplies for the FIG. 7 circuit.
Figure 12:
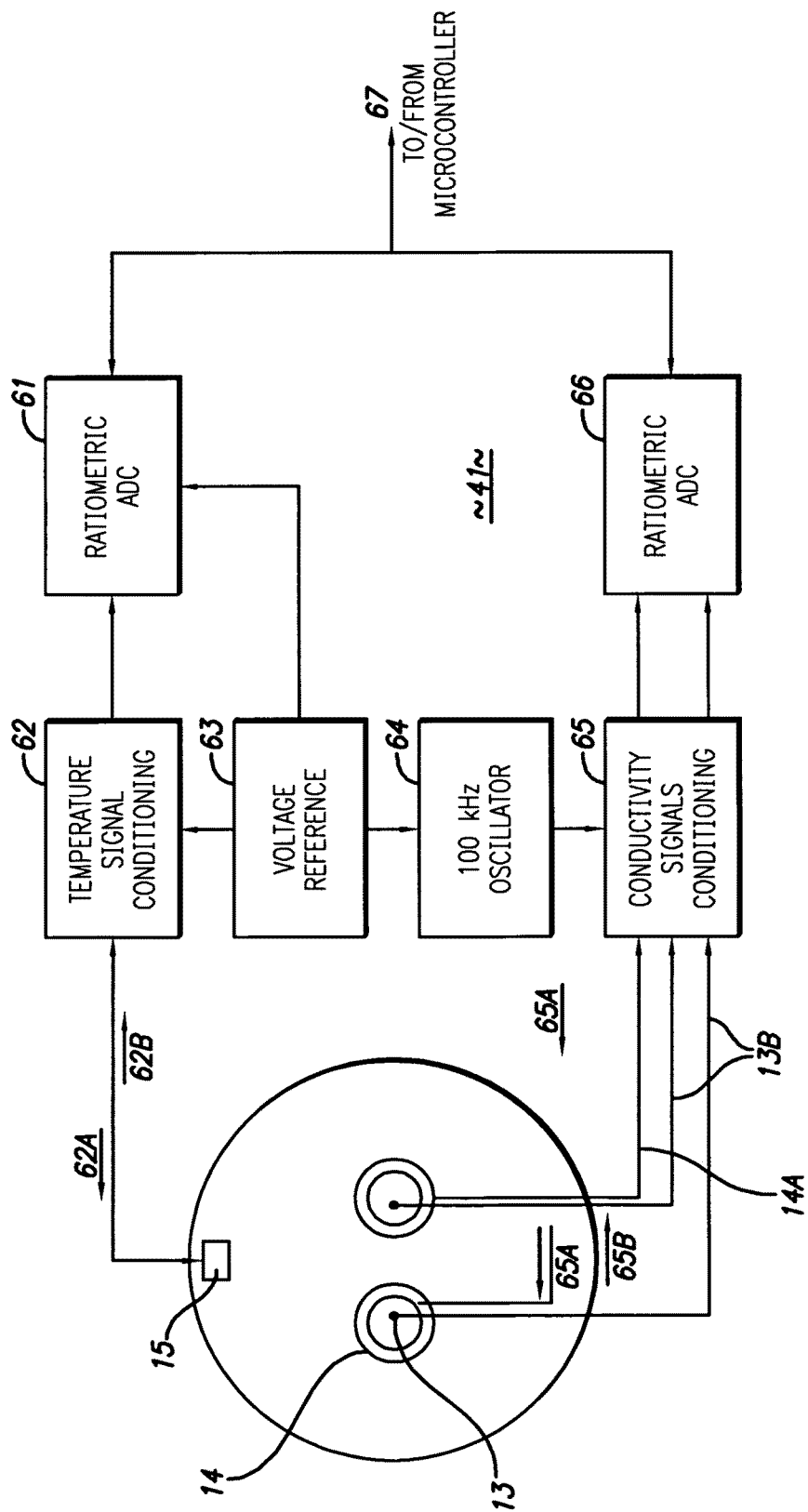
FIG. 12 is a like view but of preferred sensor-signal-conditioning and data-acquisition circuitry.

Power Supply:

A representative government-measurements oceanographic buoy (a National Data Buoy Center buoy, for example) has virtually unlimited onboard power, at 12 and 24 Vdc, as compared with the power needs of our invention. Please note that actual voltages will vary widely; these are merely examples, and only for one preexisting buoy. Preferably, we isolate and regulate power 55, 52 from such supplies 71 (FIG. 10) to produce the voltages 55, 52 necessary to operate our conductivity and temperature sensors 12-14 and 15 (FIG. 1) respectively, piezoelectric transducer 24, digital control 62-65 (FIG. 12) and serial interface 61, 66, 67.

In our preferred embodiments the serial interfacing (a task performed by a microcontroller 67) requires a single 5 Vdc supply. The sensor 13-15 requires an isolated ±5 Vdc supply. Current drawn from these supplies is rather low; together they consume less than 1 W when activated. Outputs 55, 52 (FIG. 10) of the power-isolated electronics are coupled via isolators 72, 73 to any sea-referenced electronics in the buoys.

Driving the piezoelectric transducer, however, requires significantly greater instantaneous power. At maximum drive voltages of up to ±200 V, the transducer could consume as much as 30 W, but only for short time periods and at very low duty cycles. One of many preferred embodiments incorporates drive voltages nearer to 50 V for cleaning the sensor faces. Power required varies with the square of the applied voltage; hence instantaneous power consumption is much less than 30 W.

In addition to isolation of the sensor power 52, safety and typical circuit operation call for isolation 72 of the high-voltage supply 55 too. In summary, isolated power converters 72, 73 use power from the onboard batteries 71 and convert it to the bias etc. voltages 55, 52 for the sensor electronics and the cleaner.

To avoid introducing errors into the sensor output, the ±5 V supply should be stable and free of significant ripple and noise. Since it is relatively easy with commercial d.c.-to-d.c. converters to isolate harmonics of the power-conversion frequency from harmonics of the conductivity-oscillation frequency, an inexpensive converter ordinarily suffices.

An alternative approach is to use a separate pair of batteries that is charged from the buoy batteries. In this case, the operating battery is preferably switched out of the buoy battery gang and charging circuitry when needed for measurements—or other measures taken to avoid undesired interference from the buoy battery gang and associated equipment. Achieving this is well within the state of the art.

Power to drive the piezoelectric transducer generally requires design to specification. Isolated high-voltage supplies are readily available commercially.

Piezoelectric Drive:

To obtain the greatest displacement efficiency, the piezoelectric transducer is advantageously driven by a stable frequency source at high voltage. Due to manufacturing tolerances, each piezoelectric transducer and sensor assembly has slightly different characteristics. Resonant frequencies of each transducer are therefore slightly different, and any drive design preferably takes this fact into account.

Figure 11A:
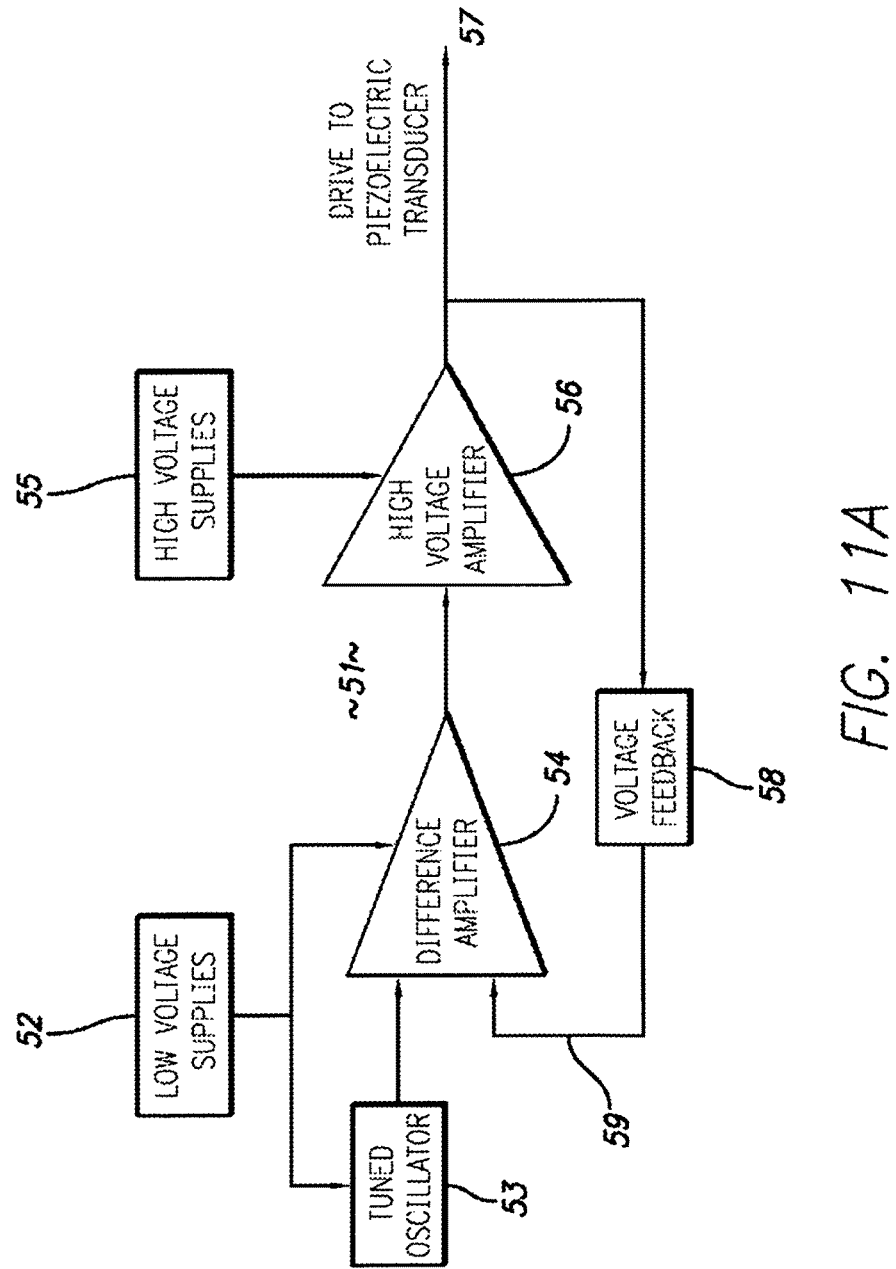
FIG. 11A is a view like FIG. 7 but of an oscillator and drive circuitry for the FIG. 1 vibration driver.
Figure 11B:
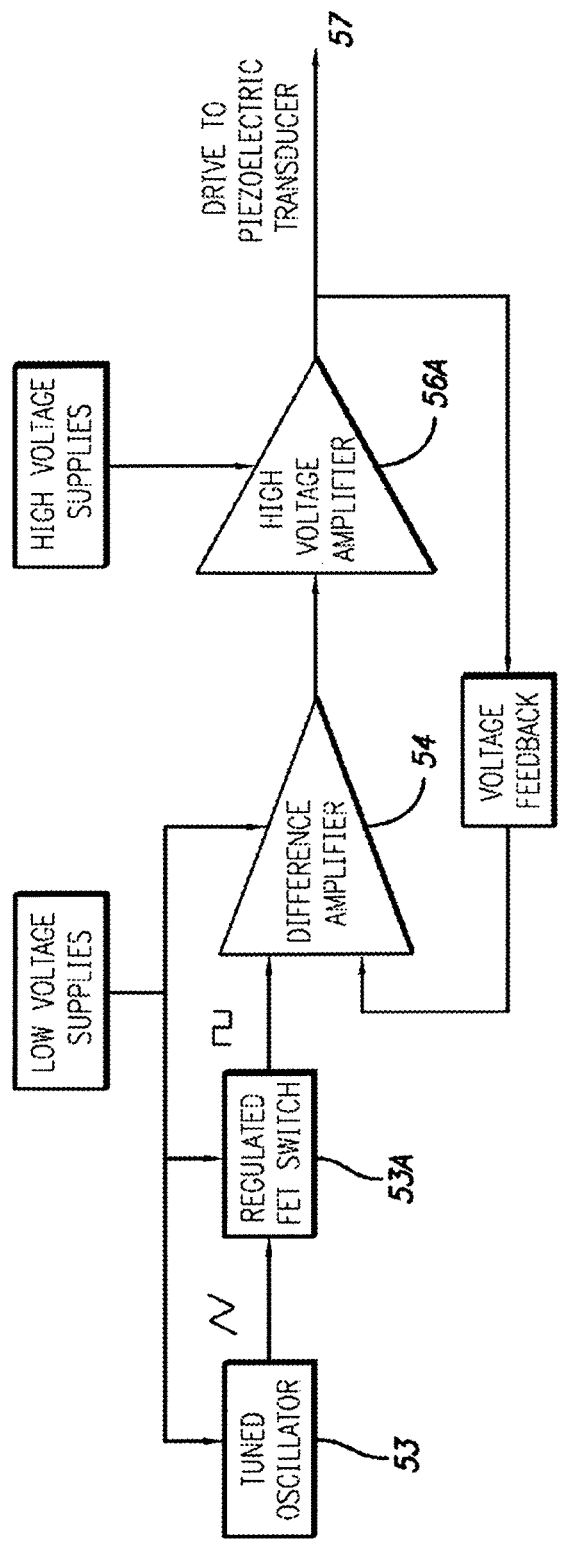
FIG. 11B is a like view but with an FET switch.

Our now-preferred embodiment includes a tunable oscillator 53 (FIG. 11) and a power amplifier 56. Isolated voltage from the local battery 71 (FIG. 10) is reduced 73 and regulated 74 to form a low-voltage supply 52 that biases the oscillator 53 (FIG. 11)—and a difference amplifier 54 fed by the oscillator. The difference amp 54 in turn feeds the oscillator 53 signal to a high-voltage power amplifier 56.

The difference amplifier serves a purpose to be more fully explained below. The battery 71 (FIG. 10) voltage is also isolated 72 to feed a high-voltage line 55 that more-directly drives the power amplifier 56 (FIG. 11), which in turn provides ultrasonic drive 57 to the transducer.

Ideally the resonant frequency for each sensor/transducer assembly is measured, and the oscillator 53 tuned to match it. One desirable way to accomplish this is to begin by preestablishing the frequency desired for organisms or other particles of expected size and other properties (e.g. cohesiveness). The next step is to design the sensor/transducer to resonate at that frequency—under anticipated standard conditions of temperature, pressure etc.

At that stage the mechanical design should also be made to hold the resonance within a range relatively near that same frequency under expected variations from those conditions. Then the overall circuitry can be designed to search automatically for natural resonance of the assembly—thereby holding the vibration at the desired frequency for standard conditions, and near that frequency for the expected variations.

Automatic fine tuning to resonant peaks is achieved using sensors, the host microcontroller 67, and suitable means for changing the frequency of the tuned oscillator 53. Sensors measure the amplitudes and relative phase of the voltage and current into the vibrating piezoelectric material 24, or directly measure the amplitude of displacement of the cleaned region 12, 112.

The measured quantities are processed in the controller 67 to recognize the desired resonant peak. The controller provides digital input to the tuned oscillator that varies the frequency over a small range that includes the resonant peak. When the peak is found, the controller holds the tuning input to the oscillator at the frequency of the peak until another tuning cycle is required.

This operation avoids the necessity for fine-tuning the circuit 51 as a part of fabrication. Perhaps more importantly, as described above it can follow the target particles through structural resonant shifts that arise in the field from environmental changes, after manufacturing is complete.

For some applications several amplifier stages are required to scale up the oscillator output, as required to drive the transducer to the desired displacement. In such designs an operational amplifier can form the first stage, followed by a common-emitter (or similar) amplifier stage to supply the necessary voltage gain, and a push-pull drive-output stage to provide a high-current output. The operational amplifier also limits the frequency response of the circuit, which is advantageous to prevent undesirable oscillation and noise sensitivity.

An alternate approach to that discussed above is to drive the ultrasonic transducer with square waves. In this case, the circuitry after the tuned oscillator 53 includes an FET switch 53A (FIG. 11B) and—following the difference amp 54—a high-power push-pull square-wave driver 56A.

Sensor Conditioning Circuit:

Preferred sensor-conditioning circuitry includes components to refine the measurements of water temperature and conductivity. The measurement results 62, 65 (FIG. 12) are converted 61, 66 to digital data and sent to a microcontroller 67.

Preferably the system has two kinds of "conditioning" 62, 65: (1) preliminarily, determining best operating parameters of the sensors (or other device) and adjusting 62A, 65A those parameters to the best values; and then, later, (2) receiving 62B, 65B and massaging any resulting output signals to optimize their use in whatever utilization apparatus 67 receives those signals. Thus as to the phrase "sensor-conditioning" the "sensor" may mean the entire package.

In our now-most-preferred sensing circuitry, a microcontroller 67 acquires data from ratiometric digitizations 61, 66 of:

the thermistor 15 voltage and the thermistor circuit bias 63, and of the conductivity-cell 13/14 current 14A (at the rings 14) and voltage 13A (across the voltage electrodes 13) in the conductivity cell.

Meanwhile the microcontroller 67 controls operation of the analog-to-digital converter (ADC) blocks 61, 66.

The thermistor bias is drawn from a voltage-reference module 63, which also supplies a 100 kHz oscillator that is mixed 65 with the signals 13A, 14A from the conductivity cell. These features optimize the digital measurement-output signals for use in the controller 67.

Details of our early experimental temperature and conductivity measurement circuits, mentioned previously, are upgraded in present practice of our invention—based upon what was learned from that earlier work. Lab equipment used to generate supply voltages and oscillator signals is replaced by dedicated circuitry. An inexpensive stable reference voltage source is most-typically adequate for the temperature sensor, and an oscillator is designed for the conductivity sensor.

Earlier circuitry is improved. We now prefer amplifiers, commercially available, which reduce small inaccuracies in gain at 100 kHz. Other available amplifiers are used to reduce offset errors in the rectifiers and filters. Use of these amplifiers prevents offset errors from significantly distorting the conductivity ratio data.

Serial Line Interface:

Preferred embodiments of the present invention are compatible with provision of telemetry or like communication links to transmit or locally record the sensor data. If desired for the particular application at hand, this feature advantageously uses a programmed microcontroller 67 (FIG. 11) to—among many other functions, some mentioned elsewhere in this document—provide a serial line interface to the collected sensor data.

The microcontroller can be, for example, a member of the inexpensive Freescale (formerly Motorola) 68HC08 family. It applies existing firmware to reformat the sensor data stream as RS-232 serial data. The digital data, on its isolated power supplies 52 (FIG. 10), is interfaced to electronics that are based on buoy power 71, with an inductive modem or an optical isolator.

With respect to our present invention, provision of a serial interface may be regarded as optional. On the other hand, given the foregoing teachings of the present invention, persons of ordinary skill in this field will now recognize that the utility of our present invention is considerably greater when data acquired by the self-cleaned sensors or other instrumentation are promptly and readily accessible. This is particularly true in view of the very extended duration of accurate deployment enabled by our present invention.

Figure 13:
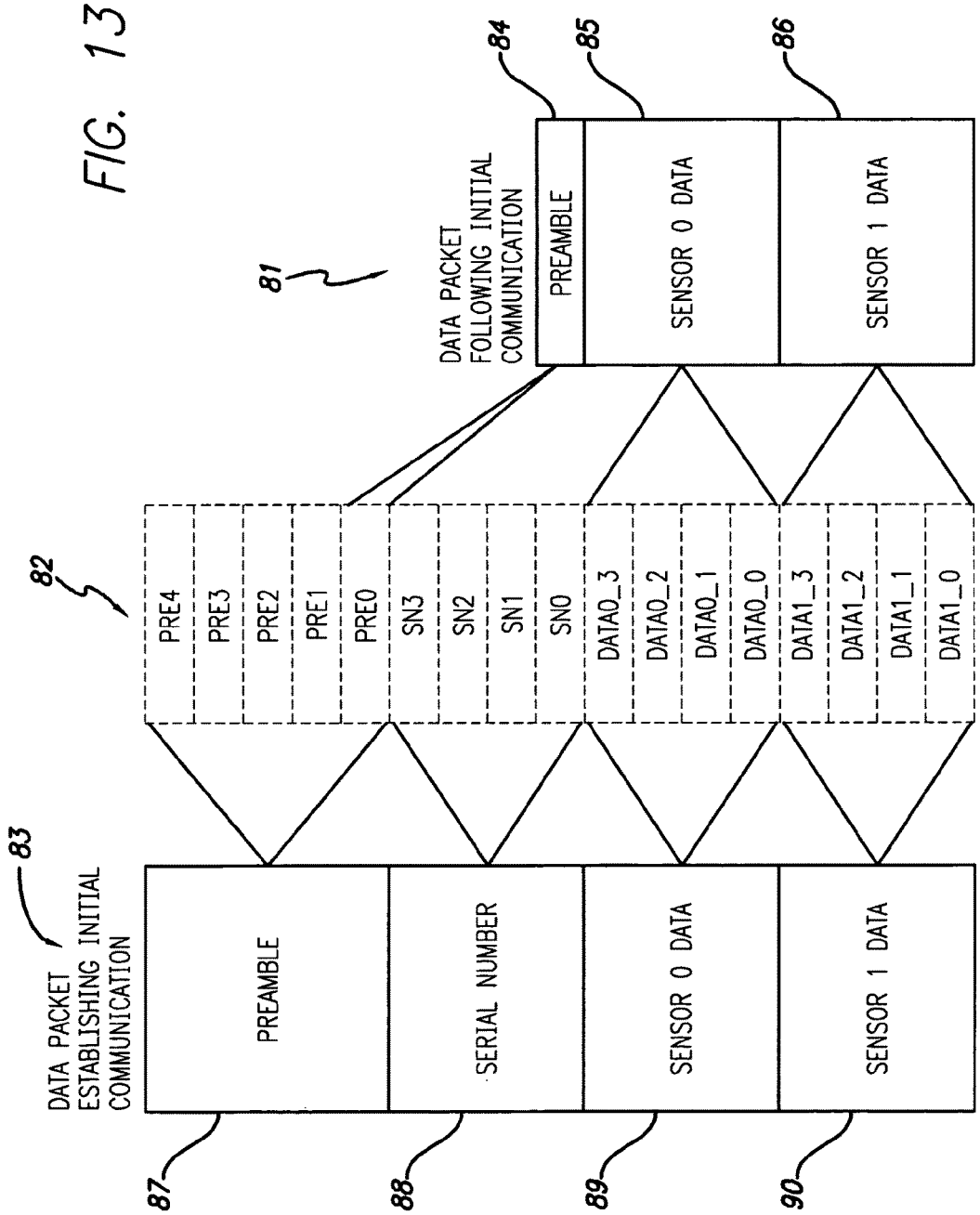
FIG. 13 is a diagram of data structures for (left-side view) "establishing initial communication between the FIG. 12 circuitry and a remote or external host computer, and for (right-side view) data transmission during data collection thereafter.

During the process of establishing communication to a host processor, 17-byte data packets 83 (FIG. 13) are transmitted to configure the communication. These data include a preamble or header 87 for identifying the start of a data set, and a sensor serial number 88 with related information for identifying and characterizing (e.g. calibrating) the sensor or sensors, and measurement data or data structures 89, 90 for plural (representatively two) sensors. (Data for just a single sensor is possible as well.)

After those initializing data, 9-byte packets 81 are transmitted to transfer the bulk of the data—including essentially only data 85, 86 for plural (again typically two) sensors. Data bits or words 82 in the two packet formats 81, 83 are mutually corresponding. Thus the microcontroller (serial interface) data stream includes the unit serial number SN0-SN3 and calibration constants.

The instantaneous data streams may contain some effects of buoy motion; therefore we prefer to program the microcontroller to average the temperature and conductivity data into quantities that reduce any such buoy effects. The data transmitted include an encoding scheme designed to detect errors in the data packets.

Figure 3:
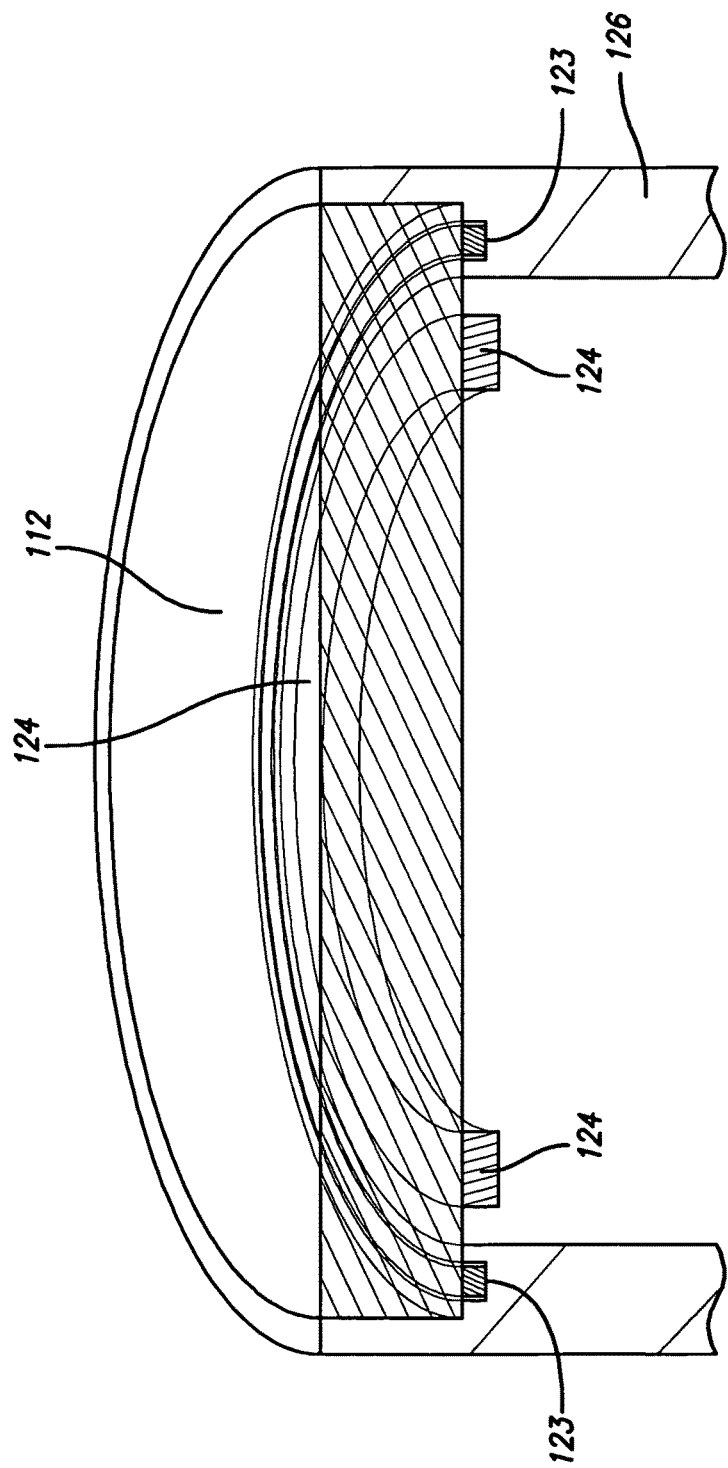
FIG. 3 is a sectional view generally like FIG. 1, but taken along a centerline and showing another preferred embodiment that is a vibrationally cleaned optical window (rather than a ceramic disc for sensing conductivity and temperature)

In addition, the microcontroller 67 (FIG. 12) controls timing and duration of the cleaning operation performed by the piezoelectric transducer 24, 124 (FIGS. 1 through 3). Microcontroller firmware (not shown) is also advantageously—but not necessarily—designed to receive user commands to initiate a cleaning, and to modify the timing and duration of regular cleanings.

PERTINENT PUBLICATIONS

These documents, arising from our partially related earlier work, are wholly incorporated by reference herein:

Farruggia, G. J., Fraser, A. B., "Miniature Towed Conductivity Apparatus," *Proceedings Of Oceans* (Sep. 10-12, 1984);

Farruggia, G. J., Fraser A. B., "Sensor and Sensor System for Liquid Conductivity, Temperature, and Depth," U.S. Pat. Nos. 6,404,204 and 6,577,134 (Jun. 11, 2002 and Jun. 10, 2003);

Fraser, A. B., "Submarine Wake Sensors," *APL Technical Review* 3, No. 1, pages 44-49 (1992);

Fraser, A. B., "Heated Element Velocimeter," U.S. Pat. No. 5,117,691; and

Fraser, A. B., "Frequency Encoding Closed Loop Circuit with Transducer," U.S. Pat. No. 4,408,169.

Enhancements and Refinements Flowing from the Present Invention:

Our versatile, nonfouling temperature/conductivity sensors can be an enabler for many related applications. By emphasizing simplicity and longevity as primary aspects of our invention from the outset, we have laid the groundwork for worthwhile improvement of analogous measurement regimens in many commercial, medical and engineering applications.

Using a ceramic substrate as a common platform technology minimizes R&D costs, allowing multiple product lines to benefit from economies of scale. Therefore, even individual low-volume applications will be realized at lower cost to the end user than has been possible heretofore.

Commercial Applications—and Software Tool:

There are many ways to use this self-cleaning instrumentation or transducer technology. Since every sensor or sensor technology requires a different piezoelectric oscillator design, the nonrecurring engineering costs may be the cost driver to outfitting any sensor with our antifouling system.

Figure 14:
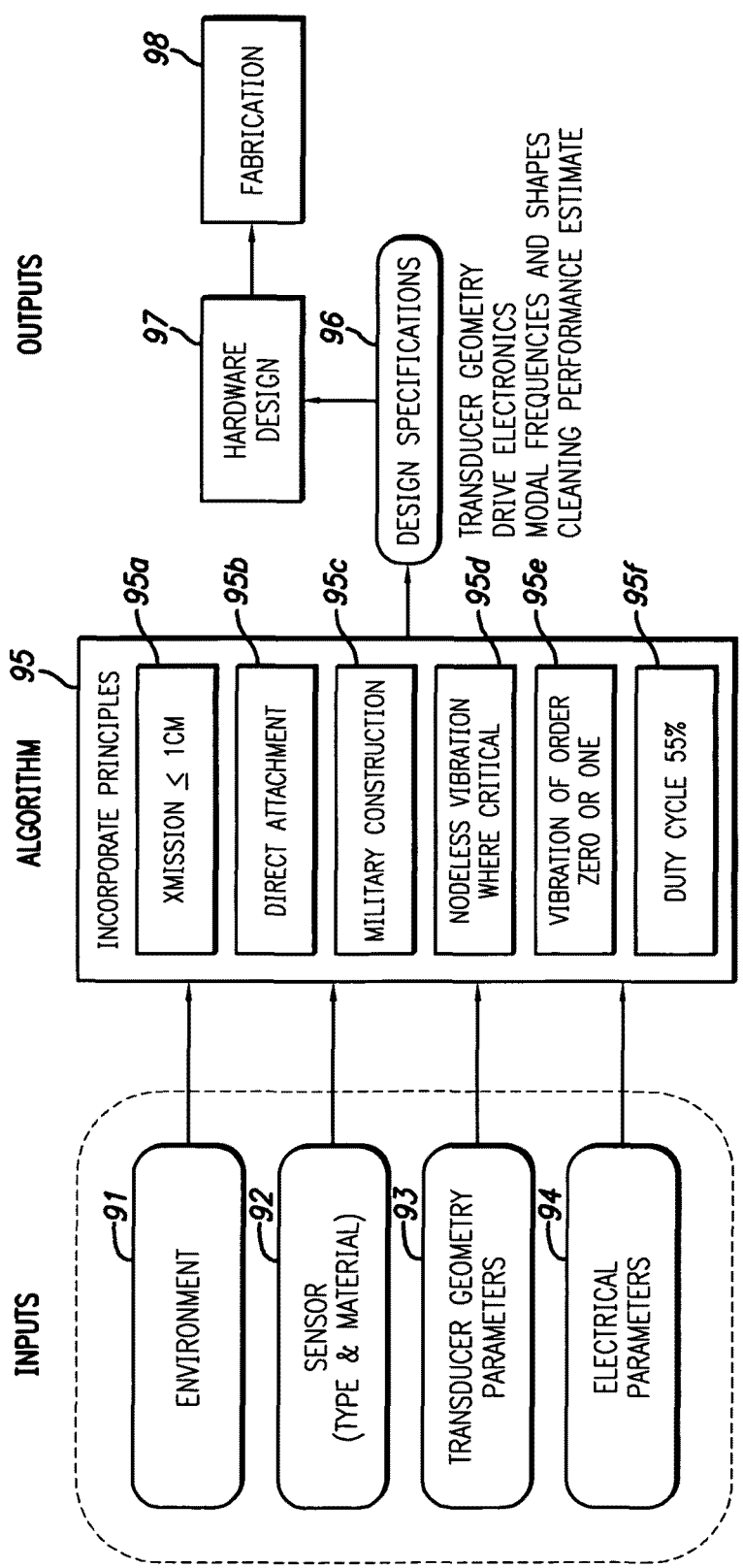
FIG. 14 is a design-and-fabrication flow chart for expediting.

To reduce these costs, our invention encompasses provision of a software tool that exploits the hardware and techniques discussed above. The software very efficiently automates a procedure 91-95 (FIG. 14) that directly generates physically usable design specifications 96.

These specs 96 in turn can interface directly to a manually performed design process 97—or to a standard computer-aided-design program 97 that designers operate to expedite such work—and in this way still further minimize future nonrecurring costs associated with each application of the technology.

Input data for the algorithm 95 of this procedure include expected operating-environment data 91, desired type and material 92 of the sensor to be cleaned, corresponding parameters 93 of the transducer (and sensor) geometry, and electrical (as well as, in appropriate cases, chemical) parameters 94.

The environmental inputs 91 define the fluid parameters, density, biofouling types and distribution, temperature and pressure range and any other relevant environmental parameters. The sensor or critical surface 92 defines the parameters of the surface to be kept clean. The material type, stiffness, physical dimensions, dimensional constraints (boundary conditions, open areas etc.) are examples of this input to the algorithm.

The "corresponding parameters 93" include transducer geometry parameters, e.g. oscillator materials, attachment options, size and weight considerations, and available space within existing sensors or devices to retrofit the critical surface. The electrical parameters 94 define drive circuitry for the oscillator—particularly circuitry best suited for the newly designed or retrofitted situation.

The algorithm 95 accepts these inputs and applies the principles and preferences 95*a-f* set forth in this document to develop the best path through the matrix—for defining the specifications 96 for the oscillator choice, attachment, drive circuits, and output-model analysis of modal structure for the integrated system. These outputs lead directly to and through the hardware design 97 and subsequent fabrication 98.

Output specifications 96 include specific transducer geometry and other parameters, circuit parameters for drive electronics, and modal frequencies and shapes. Advantageously the output design specifications further include estimates of cleaning performance for the finished apparatus manufactured according to the design. The overall process also includes physically manufacturing 98 mechanical, electrical and optical components, modules and completed assemblies, and supplying them for field use.

We can use the software tool ourselves to efficiently design, make and supply new sensors, or custom-designed components for integration into sensors made by others. Alternatively or additionally, the transducer-design software itself can also be distributed commercially or otherwise. It can be used by sensor vendors to facilitate their own design and fabrication efforts.

New and unobvious features of our invention include, without limitation, the nature of our conductivity-sensor head, and high drive frequency to eliminate the need for platinization (and thus nonreliance on use of platinum black), and also the concept of using an ultrasonic source (particularly but not necessarily a piezotransducer or electromagnetic shaker, or in principle even an electrostatic one, or a mechanical system such as a MEMS driver or other machine) embedded or otherwise incorporated to clean instrumentation including but not limited to oceanographic sensors and the several other applications mentioned earlier, are all believed to be new and unobvious. They are by no means, however, the only new, unobvious and useful aspects of our invention.

The sensor of our invention has advantages over the previously mentioned technologies in cost and longevity of measurements on-station. Some competing sensors may have better inherent accuracy at the outset, but fail to prevent degradation due to fouling. Our sensing head takes advantage of the use of ceramic circuit-board technology, which is mass producible, and is therefore less expensive in large quantities.

Figure 15A:
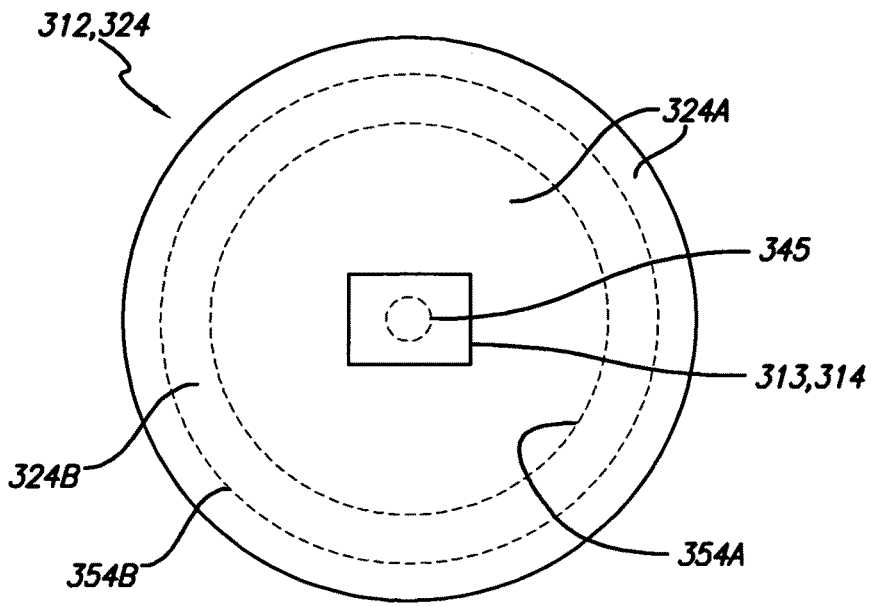
FIG. 15A is a top plan of the FIG. 15 head (likewise partially shown in the broken line)
Figure 15:
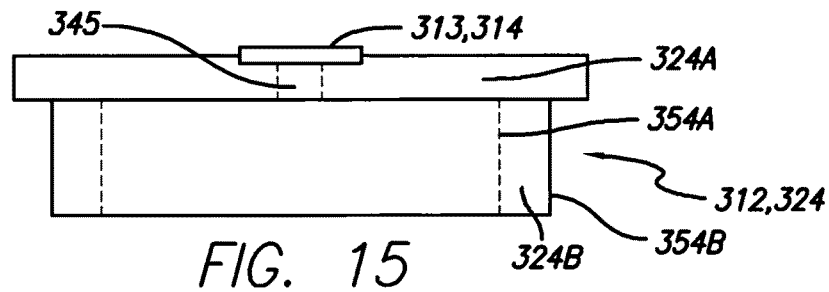
FIG. 15 is an exterior side elevation (with internal surfaces shown in the broken line) of a vibrating device head very generally analogous to that of FIG. 1 but not necessarily for a sensor—and here the device that is vibrated is unitary with the mechanical vibratory driver.
Figure 15B:
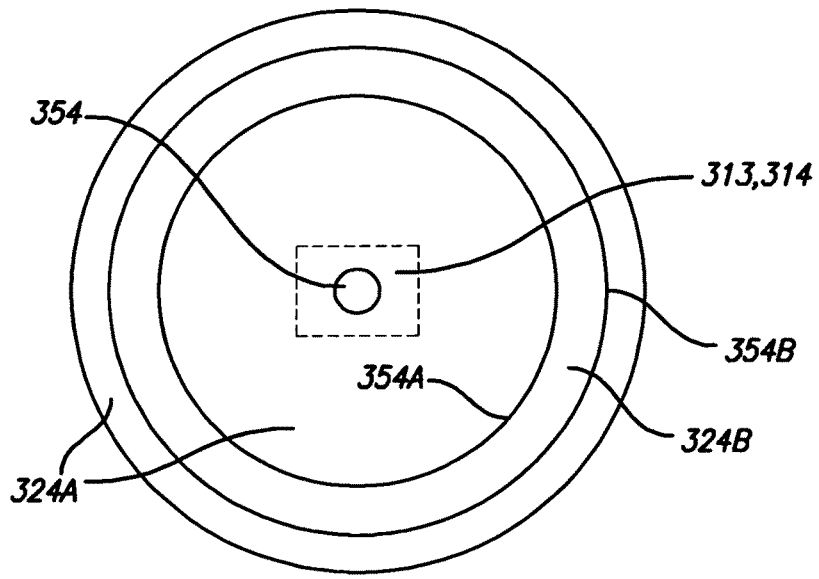
FIG. 15B is a like bottom plan of that same head.

In our preferred unitary embodiment, mentioned previously, the integral top pad 313/314 (FIGS. 15, 15A, 15B) corresponds to the like-numbered rings and discs 13, 14, 213, 214 of other embodiments discussed above—if the instrument is a conductivity/temperature sensor—or otherwise corresponds to windows or other features as in earlier-detailed configurations. Similar rings and discs, or other functional elements if preferred, are integrated into the pad 313/314 to perform primary functions of the instrument. Sensor or other leads etc. may pass through the "via" 345.

In this construction the cylindrical table 324A and annular pedestal 324B are also preferably integrated with the pad 313/314 to form a unitary, or monolithic (I.e. all one piece) piezo structure—which corresponds to the like-numbered piezo transducer 24 or 124 discussed earlier. Here, however, these piezoelements are advantageously unitary with the primary-function elements 313/314.

Figure 8:
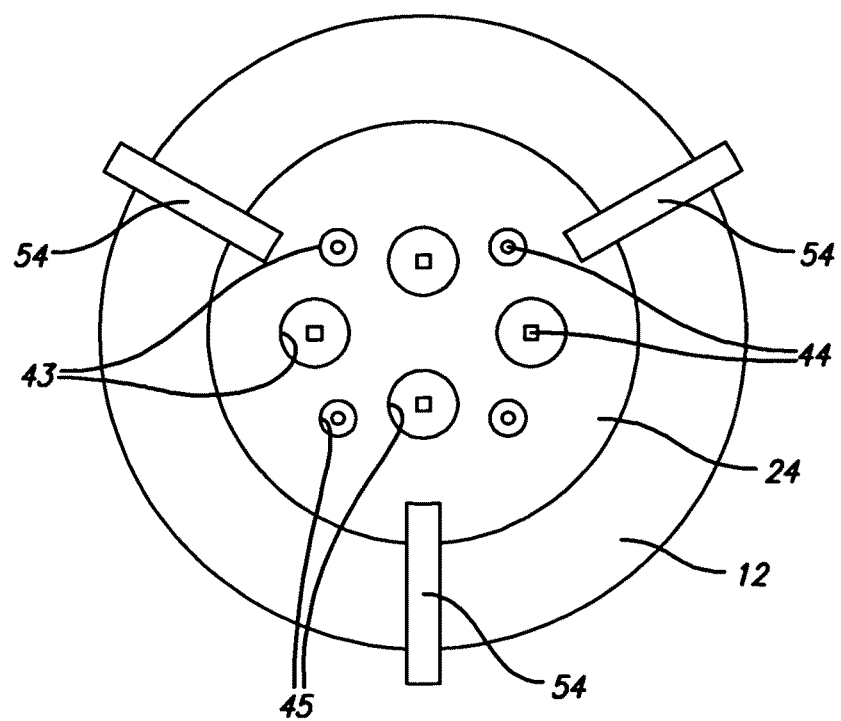
FIG. 8 is a bottom plan like FIG. 6 but of a generally representative sensor disc and vibrational driver used in some experimental prototypes of our invention.

The interior and exterior annular faces 354A, 354B of the annular piezoelectric pedestal 324 are electrically conductive, and in a very general sense correspond functionally to the previously discussed, like-numbered conductive tabs 54 (FIG. 8). More specifically, a varying electrical voltage is applied across (or "between") the two conductive annuli 354A, 354B—causing varying, vibratory piezoelectric deformation of the entire structure 312/324. Such deformation is activated periodically or from time to time, as desired, in very generally the same way as set forth for the vibrating structures discussed earlier in this document.

The foregoing disclosure is exemplary, and should not be taken to limit the scope of the invention—which is to be determined by the appended claims.

We claim:

1. Apparatus for use with a device that has an exposed window surface, or an exposed active transducing surface that is part of a transducer and is outside any sealed chamber that may be associated with the device, and is (a) critical to performance of the device and (b) operated at least partially submerged within and in direct contact with an aqueous medium and (c) susceptible to biofouling; said apparatus comprising:
    an ultrasonic cleaning system operative at a frequency or frequencies in a range of approximately twenty kilohertz to nearly four hundred kilohertz; and
    means for substantially directly fixing the system to or integrating the system into such critical surface, to vibrate such surface and thereby reduce or substantially eliminate biofouling of such surface, particularly formation of biofilm on such surface.

2. In combination, the apparatus of claim 1 together with:
    such device, including such critical surface; and wherein said surface is a rigid-window surface, and transmits electromagnetic radiation or acoustic vibration; and
    the fixing or integrating means fix the system to or integrate the system into such surface at a part of the device that is behind the exposed window surface.

3. In combination, the apparatus of claim 1 together with:
    such device, including such critical surface; and wherein said transducing surface is in direct contact with such aqueous medium outside any such sealed chamber;
    said transducing surface interacts directly with a characteristic or constituent of such aqueous medium to develop signals indicative of a parameter of such characteristic or constituent; and
    the fixing or integrating means fix the system to or integrate the system into such surface at a part of the device that is behind the exposed transducing surface.

4. The apparatus of claim 3, wherein:
    such constituent is a chemical species;
    such parameter is such concentration of such species;
    the active transducing surface interacts directly with the chemical species in such aqueous medium electrochemically, to develop signals indicative of such concentration of such species;
    the transducer has electrodes, which also are exposed in the aqueous medium and susceptible to biofouling; and
    the cleaning system reduces or substantially eliminates biofouling of the electrodes in addition to biofouling of the surface.

5. The apparatus of claim 1, wherein:
    the cleaning system is substantially unitary with such device.

6. The apparatus of claim 1, wherein:
    the fixing-or-integrating means comprise a substantially solid vibration-transmitting structure intermediate between such surface and the cleaning system.

7. The apparatus of claim 6, wherein:
    the structure comprises a mounting plate fixed between such surface and the cleaning system.

8. The apparatus of claim 1, wherein:
    the fixing-or-integrating means comprise a coupling gel or adhesive for transferring vibration from the cleaning system to such surface.

9. The apparatus of claim 1, wherein the fixing-or-integrating means comprise:
    a substantially solid intermediate structure; and
    a coupling gel or adhesive for transferring vibration from the cleaning system to such surface.

10. The apparatus of claim 1, wherein:
    the fixing-or-integrating means are not for transmitting vibration to such surface through aqueous medium that surrounds such surface.

11. The apparatus of claim 1, wherein such device is selected from the group consisting of:
    an electrical- or thermal-conductivity sensor;
    a sensor of oxygen or pH, or other chemical sensor;
    a window for passing electromagnetic radiation;
    a compressive-wave transducer that is not itself self cleaning;
    a solar panel; and
    an antenna.

12. The apparatus of claim 11, wherein:
    such device is a window or other element, at least part of which is not to be obstructed; and
    the ultrasonic cleaning system comprises an ultrasonic element that is:
        toroidal and positioned generally at the periphery of such window or other element, or otherwise peripheral to such window or other element, and
        does not obstruct such not-to-be-obstructed part of such window or other element.

13. The apparatus of claim 11, wherein:
    such surface can be obstructed without impairing its function; and
    the ultrasonic cleaning system comprises an ultrasonic element that is for mounting generally centrally to such surface.

14. The apparatus of claim 1, wherein the ultrasonic cleaning system comprises a driver selected from the group consisting of:
    a piezotransducer operative at a frequency or frequencies in a first range of approximately fifty kilohertz to nearly four hundred kilohertz;
    an electrostatic driver operative at a frequency or frequencies in a second range of approximately twenty to fifty kilohertz;

an electromagnetic driver operative in said second range; and a microelectromechanical drive, or other mechanical machine, operative in said second range.

15. The apparatus of claim 14, wherein:

the piezotransducer is piezoceramic;

changes in dimension within the piezoceramic are at least as large as thickening or thinning of the piezoceramic during vibration; and the piezoceramic piezotransducer has relatively higher mass than piezofilm piezotransducers have, and provides higher amplitude of vibration in such surface than possible using a piezofilm piezotransducer.

16. The apparatus of claim 1, wherein:

such exposed transducing surface comprises or is part of a conductivity sensor or electrochemical sensor that is not sealed by a membrane; and the ultrasonic cleaning system and fixing-or-integrating means comprise means for vibrating such surface.

17. The apparatus of claim 16, wherein:

such conductivity sensor is substantially planar.

18. The apparatus of claim 16, wherein:

such conductivity sensor is built upon a ceramic substrate.

19. The apparatus of claim 1, wherein:

such device comprises a conductivity-measuring cell that has one or more sensing elements and senses impedance of a sensing element, or impedance between pairs of sensing elements or among groups of sensing elements, as immersed in a medium.

20. The apparatus of claim 19, wherein such conductivity-measuring cell determines a ratio between:

a voltage impressed across the cell, and a resulting current through the cell; or a current forced through the cell, and a resulting voltage across the cell.

21. The apparatus of claim 1, wherein:

such surface has a functional region; and the ultrasonic cleaning system and fixing-or-integrating means comprise means for vibrating such functional region of such surface in a vibrational mode whose amplitude is high enough, throughout such functional region, to effectively reduce or substantially eliminate biofouling in such functional region.

22. The apparatus of claim 21, wherein:

the vibrational mode has substantially no node within such functional region.

23. The apparatus of claim 1, wherein:

such surface has a functional region generally at or near a center of such surface; and the ultrasonic cleaning system and fixing-or-integrating means comprise means for vibrating such generally central functional region in a fundamental mode, to effectively reduce or substantially eliminate biofouling in such generally central functional region.

24. The apparatus of claim 1, wherein:

the ultrasonic cleaning system and fixing-or-integrating means comprise means for vibrating such surface in a zero-order mode, to effectively reduce or substantially eliminate biofouling throughout such surface.

25. The apparatus of claim 1, wherein:

the ultrasonic cleaning system and fixing-or-integrating means comprise means for vibrating such surface in a plurality of modes, simultaneously or separately;

wherein, in combination the plurality of modes provide effective cleaning across at least a region of such surface.

26. The apparatus of claim 25 wherein:

such surface is mounted between two compliant elements to oscillate separately from other mounting parts of the apparatus.

27. The apparatus of claim 1, further comprising:

means for searching for a natural resonance of such active transducing surface, as mounted.

28. The apparatus of claim 1, wherein:

the ultrasonic cleaning system and fixing-or-integrating means comprise means for vibrating such surface at a duty cycle that is on the order of five percent, or less.

29. The apparatus of claim 1, wherein:

the ultrasonic cleaning system and fixing-or-integrating means comprise means for vibrating such surface at a duty cycle that is on the order of one-tenth percent, or less.

30. The apparatus of claim 1:

further comprising means defining a waterproof chamber whose interior is generally at or near atmospheric pressure; and wherein:

such active transducing surface forms part of an external wall of the chamber and is, apart from remoteness and expense, substantially accessible; and such active transducing surface is not within the chamber.

31. The apparatus of claim 30, wherein:

the waterproof chamber contains a circuit or vibrating element, or both, of the ultrasonic cleaning system.

32. The apparatus of claim 1, further comprising:

means for determining ideal operating conditions of such device; and means for automatically adjusting operating conditions of such device to substantially said determined ideal conditions.

33. The apparatus of claim 1, further comprising:

means for operating the cleaning system, to reduce or substantially eliminate such biofouling, when the active transducing surface is no longer submerged within the aqueous medium.

34. The apparatus of claim 1, wherein:

such surface forms a periscope window for a craft or other apparatus that sometimes operates submerged in an aqueous medium; and the operating means comprise means for vibrating such surface, selectively:

while the sometimes-submerged craft or other apparatus is submerged in the aqueous medium; or after the sometimes-submerged craft or other apparatus comes to the surface of the aqueous medium.

35. The apparatus of claim 1, further comprising:

means for operating the cleaning system at one or more frequencies determined from particle size of fouling material to be reduced or substantially eliminated.

36. The apparatus of claim 35, wherein:

the operating means comprise means for searching for natural resonance associated with such particle size.

37. Apparatus for use with a device that has an exposed window surface, or an exposed active transducing surface that is part of a transducer and is outside any sealed chamber that may be associated with the device, and is (a) critical to performance of the device and (b) operated at least partially immersed within and in direct contact with a liquid and (c) susceptible to undesirable chemical deposition on the surface; said apparatus comprising:

an ultrasonic cleaning system operative at a frequency or frequencies in a range of approximately fifty kilohertz to eighty kilohertz; and means for substantially directly fixing the system to or integrating the system into such critical surface, to vibrate such surface and thereby reduce or substantially eliminate such chemical deposition.

38. In combination, the apparatus of claim 37 together with:
such device, including such critical surface; and wherein
said surface is a rigid-window surface, and transmits electromagnetic radiation or acoustic vibration; and
the fixing or integrating means fix the system to or integrate the system into such surface at a part of the device that is behind the exposed surface.

39. In combination, the apparatus of claim 37 together with:
such device, including such surface; and wherein
said surface is an active transducing surface in direct contact with such liquid outside any such sealed chamber;
said transducing surface interacts directly with a characteristic or constituent of such liquid to develop signals indicative of a parameter of such characteristic or constituent.

40. The apparatus of claim 39, wherein:
such constituent is a chemical species;
such parameter is such concentration of such species; and
the active transducing surface interacts directly with the chemical species in such liquid electrochemically, to develop signals indicative of such concentration of such species;
the transducer has electrodes, which also are exposed in the liquid outside any such chamber and susceptible to undesirable chemical deposition; and
the cleaning system reduces or substantially eliminates chemical deposition on the electrodes in addition to chemical deposition on the surface.

41. The apparatus of claim 37:
further comprising means defining a liquid-proof chamber whose interior is generally at or near atmospheric pressure; and wherein:
such critical surface forms part of an external wall of the chamber and is, apart from remoteness and expense, substantially accessible; and
such electrodes are not within the chamber.

42. The apparatus of claim 40, wherein:
the device is particularly susceptible to undesirable deposition of calcium carbonate.

43. The apparatus of claim 37, wherein:
the fixing-or-integrating means comprise a substantially solid vibration-transmitting structure intermediate between such surface and the cleaning system.

44. The apparatus of claim 37, wherein:
the fixing-or-integrating means comprise a coupling gel or adhesive for transferring vibration from the cleaning system to such surface.

45. The apparatus of claim 37, wherein:
the fixing-or-integrating means comprise a portion of such device.

46. The apparatus of claim 37, wherein the ultrasonic cleaning system comprises a driver selected from the group consisting of:
operative at a frequency or frequencies in a first range of approximately fifty kilohertz to nearly four hundred kilohertz, a piezotransducer; and
operative at a frequency or frequencies in a second range of approximately twenty to fifty kilohertz:
an electrostatic driver;
an electromagnetic driver; and
a microelectromechanical drive, or other mechanical machine.

47. The apparatus of claim 37, further comprising:
means for operating the cleaning system, to reduce or substantially eliminate such chemical deposition, when the surface is no longer in the liquid.

48. The apparatus of claim 37, wherein:
such surface forms a periscope window for a craft or other apparatus that sometimes operates submerged in liquid; and
the operating means comprise means for vibrating such surface, selectively:
while the sometimes-submerged craft or other apparatus is submerged in the liquid; or
after the sometimes-submerged craft or other apparatus comes to the surface of the liquid.

49. The apparatus of claim 37, wherein:
such surface has a functional region;
the ultrasonic cleaning system and fixing-or-integrating means comprise means for vibrating such functional region of such surface in a vibrational mode whose amplitude is high enough, throughout such functional region, to effectively reduce or substantially eliminate biofouling in such functional region; and
such surface is mounted between two compliant elements to oscillate separately from other mounting parts of the apparatus.

50. The apparatus of claim 49, further comprising:
means for searching for one or more natural resonances of such surface, as mounted.

51. The apparatus of claim 37:
wherein such surface has a design level of performance;
wherein the ultrasonic cleaning system and fixing-or-integrating means comprise means for vibrating such surface at a duty cycle that is automatically variable; and
further comprising means for automatically controlling the variable duty cycle to clean such surface to at least said design level of performance.

52. The apparatus of claim 37, further comprising:
means for operating the cleaning system at one or more frequencies determined from particle size of chemical deposition to be reduced or substantially eliminated.

53. The apparatus of claim 52, wherein:
the operating means comprise means for searching for natural resonance associated with such particle size.

54. Conductivity-measuring apparatus comprising:
a generally planar sensing-cell surface that, at least when operating, is exposed in an aqueous medium; and
disposed on the generally planar surface:
plural ring-shaped current-drive electrodes, and
voltage-sensing electrodes, each disposed within a respective one of the drive electrodes;
said voltage electrodes being offset, toward each other in pairs, from respective centers of the current electrodes.

55. The apparatus of claim 54, wherein:
the current electrodes are roughly equidistant from a centerline or centerpoint of the surface.

56. The apparatus of claim 54, wherein:
the current electrodes are arranged in one or more groups, the current electrodes of each group being roughly equal in size and roughly equidistant from a centerline or centerpoint of the surface.

57. The apparatus of claim 54, wherein:
the ring-shaped current electrodes are arranged in two or more pairs, the electrodes of each pair being roughly equal in size and roughly equidistant from a centerline of the surface;

whereby the current electrodes of each pair establish a respective dipole-like electrical field; and the sensing electrodes are offset toward each other to locate them substantially at a zero-gradient area of the respective dipole-like electrical field of the corresponding current electrodes.

58. The apparatus of claim 54, wherein:

there are exactly two current electrodes; and the current electrodes are roughly equal in size and roughly equidistant from a centerline of the surface.

59. The apparatus of claim 54, for operation in an aqueous medium and susceptible to biofouling; and further comprising:

means for vibrating the sensing-cell surface to reduce or substantially eliminate biofouling of the surface.

60. The apparatus of claim 59, wherein:

the vibrating means are fixed substantially directly to, or substantially integrated into, the surface, at a part of the device that is behind the surface.

61. The apparatus of claim 54, wherein the measuring apparatus determines a ratio between:

a current directed through the cell; and a resulting voltage across the cell.

62. A method of designing a self-cleaning instrument that performs said cleaning by vibration to deter underwater biofouling or chemical deposition; said method comprising the steps of:

defining a set of inputs characterizing vibration constraints applicable to generally all said self-cleaning instruments;

defining an algorithm generically relating the operating inputs to design specifications of said instruments;

receiving a set of values of said inputs for a particular desired instrument; and based on the values, automatically performing the defined algorithm to compute and provide design-specification values used in designing the particular self-cleaning instrument;

wherein the performing step comprises applying at least one of these design principles:

vibration transmission, from transmitter to critical article to be cleaned, through distance on the order of one centimeter, or less, preferably substantially direct attachment of vibration transmitter to critical article to be cleaned, preferably substantially unitary construction of vibration transmitter with critical article to be cleaned, substantially nodeless vibration in critical areas, preferably vibration in order zero or one, and duty cycle of five percent or less.

63. The method of claim 62, further comprising the step of:

designing the instrument generally according to the provided design-specification values.

64. In combination with the method of claim 63, the further step of:

building the instrument, as designed generally according to the provided design-specification values.

65. The method of claim 64, wherein the set of operating parameters comprises at least some of these:

instrument type, and materials of construction;

geometry, size, weight, and optical, chemical and electrical requirements of an instrument, and of its surface or surfaces to be cleaned; and environmental conditions under which the instrument will operate.

66. The method of claim 65, wherein the set of design specifications comprises at least some of these:

vibration-driver type, material of construction, size, geometry, power, and optical details;

modal frequencies and shapes;

electronic or other drive-circuit details; and a cleaning-performance estimate.

67. The method of claim 62, wherein the set of design specifications comprises at least some of these:

vibration-driver type, material of construction, size, geometry, power, and optical details;

modal frequencies and shapes;

electronic or other drive-circuit details; and a cleaning-performance estimate.

* * * * *